United States Patent [19]

McCroskey et al.

[11] Patent Number: 5,023,895
[45] Date of Patent: Jun. 11, 1991

[54] THREE DIMENSIONAL TOMOGRAPHIC SYSTEM

[75] Inventors: William K. McCroskey, Solon; David S. Vickers, Macedonia, both of Ohio

[73] Assignee: Innovative Imaging Systems, Inc., Cleveland, Ohio

[21] Appl. No.: 317,767

[22] Filed: Mar. 2, 1989

[51] Int. Cl.$^5$ .................... A61B 6/00; H05G 1/02; G03B 42/02
[52] U.S. Cl. ............................. 378/4; 378/10; 378/8; 378/20; 378/21; 378/22; 378/195; 378/177
[58] Field of Search .................... 378/21–25, 378/28, 29, 4, 178, 20, 27, 69, 26, 10, 901, 17, 16, 168

[56] References Cited

U.S. PATENT DOCUMENTS

| | | | |
|---|---|---|---|
| 3,758,723 | 9/1973 | Green et al. | 178/6.8 |
| 3,873,834 | 3/1975 | Dammann et al. | 378/23 |
| 3,881,110 | 4/1975 | Hounsfield et al. | 250/360 |
| 4,263,513 | 4/1981 | Palluet | 378/168 |
| 4,288,695 | 9/1981 | Walters et al. | 250/445 T |
| 4,298,800 | 11/1981 | Goldman | 250/445 T |
| 4,304,999 | 12/1981 | Richey et al. | 250/445 T |
| 4,404,469 | 9/1983 | Yin | 250/363 R |
| 4,422,177 | 12/1983 | Mastronardi et al. | 378/208 |
| 4,466,112 | 8/1984 | Covic et al. | 378/7 |
| 4,491,956 | 1/1985 | Winnek | 378/41 |
| 4,503,331 | 3/1985 | Kovacs, Jr. et al. | 250/363 S |
| 4,506,327 | 3/1985 | Tam | 364/414 |
| 4,672,649 | 6/1987 | Rutt | 378/10 |

FOREIGN PATENT DOCUMENTS 0117175  8/1984  Japan ..................... 378/22

OTHER PUBLICATIONS

"Cone Beam Reconstruction With Sources On A Curve" by David V. Finch, pp. 665–673.
"Reconstruction Methods For Cone-Beam Imaging" by Bruce D. Smith.
"The Generalized Back Projection Theorem For Cone Beam Reconstruction" by Francoise C. Peyrin, IEEE Transactions on Nuclear Science, vol. NS-32, No. 4.
"An Inversion Formula For Cone-Beam Reconstruction" by Heang K. Tuy.
Practical Cone Beam Algorithm by L. A. Feldkamp et al. from Journal of the Optical Society of America dated 1984.
Article entitled "High-Speed Three-Dimensional X-Ray Computed Tomography: The Dynamic Spatial Reconstruction" by Robb et al. from The Proceedings of the IEEE dated 1983.

*Primary Examiner*—Edward P. Westin
*Assistant Examiner*—Don Wong
*Attorney, Agent, or Firm*—Renner, Otto, Boisselle & Sklar

[57] ABSTRACT

An industrial CT system is provided for three dimensional imaginig which includes a three dimensional cone beam of hard radiation fixed with respect to a two dimensional scintillation detector array. The object is positioned on a turntable interposed between the radition source and detector array. Data from two dimensional views are stored as the object is rotated on the turntable about a fixed axis. The data is sufficient upon completion of one revolution to construct a transparent three dimensional image of the object. A positioning encoding arrangement adjusts for variations in the object's mass density to optimize scan-compute times while enhancing image resolution.

23 Claims, 8 Drawing Sheets

FIG. 7

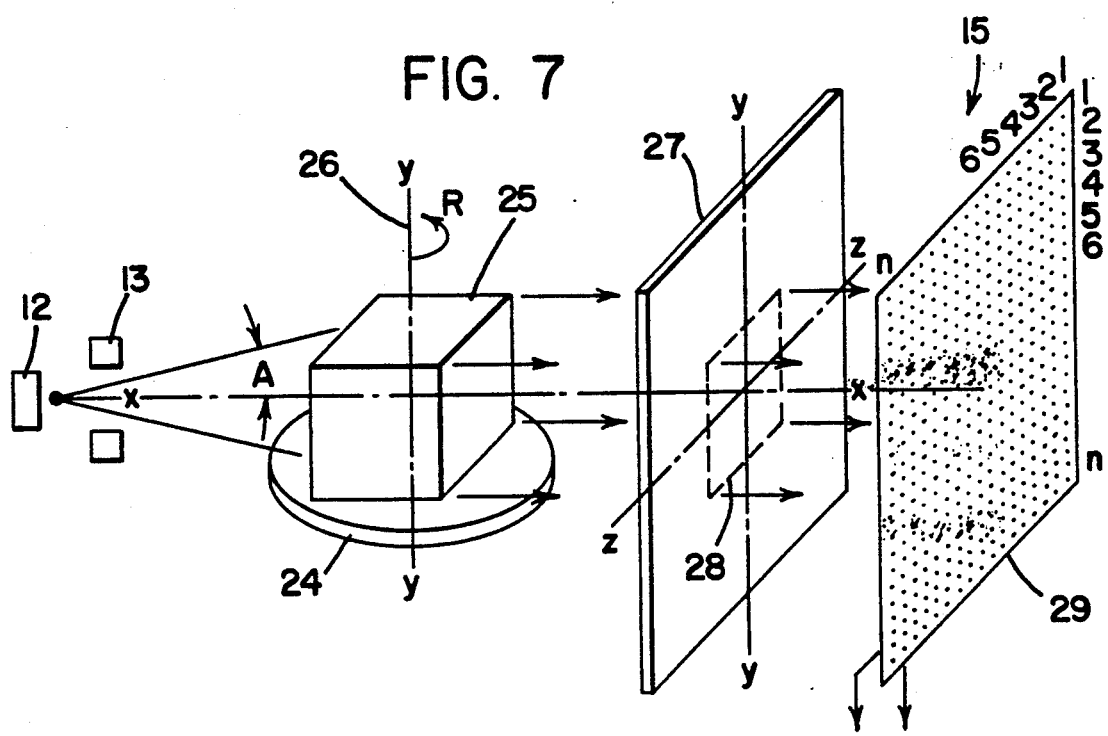
FIG. 7
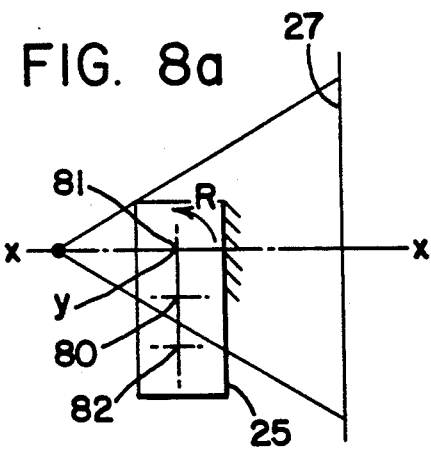
FIG. 8a
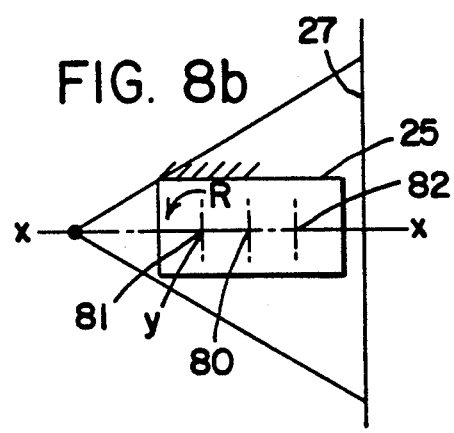
FIG. 8b
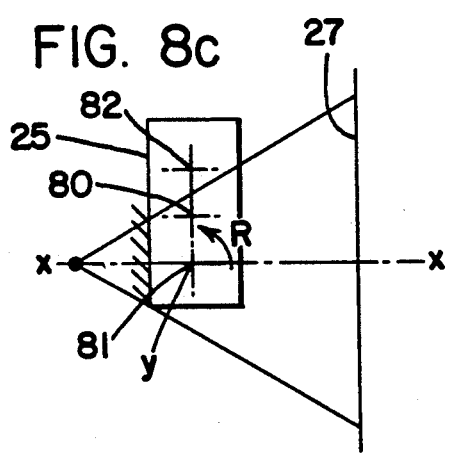
FIG. 8c
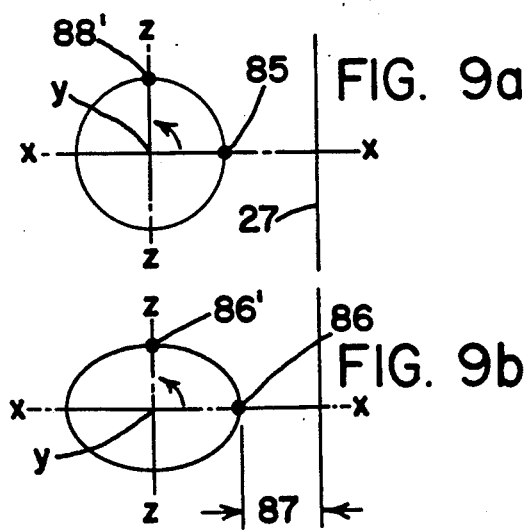
FIG. 9a
FIG. 9b

THREE DIMENSIONAL TOMOGRAPHIC SYSTEM

This invention relates generally to computerized tomographic systems and more particularly to such systems designed specifically for industrial applications.

The invention is particularly applicable to three dimensional transparent images produced by computed tomographic inspection systems for industrial applications and will be described with particular reference thereto. However, it will be appreciated by those skilled in the art that the invention can also be used to develop two dimensional images through any cross-sectional plane of the irradiated object as well as three dimensional exterior dimensioning.

INCORPORATION BY REFERENCE

The following material is incorporated herein by reference:
a) An article entitled "Practical Cone-Beam Algorithm" by L. A. Feldkamp et al, reprinted from *Journal of the Optical Society of America A*, Vol. 1, page 612, June 1984 issue;
b) An article entitled "High-Speed, Three Dimensional X-Ray Computed Tomography: The Dynamic Spatial Reconstructor" by Robb et al, published in *PROCEEDINGS OF THE IEEE*, Vol. 71, No. 3, March, 1983;
c) Green U.S. Pat. No. 3,758,723 dated Sept. 11, 1973;
d) Hounsfield U.S. Pat. No. 3,881,110 dated Apr. 29, 1975;
e) Walters U.S. Pat. No. 4,288,695 dated Sept. 8, 1981.
f) Goldman U.S. Pat. No. 4,298,800 dated Nov. 3, 1981;
g) Covic U.S. Pat. No. 4,466,112 dated Aug. 14, 1984;
n) Tom U.S. Pat. No. 4,506,327 dated Mar. 19, 1985.

BACKGROUND OF THE INVENTION

A. The Medical Field

Generally speaking, computerized tomography is a modern technique initially developed for use in the medical field to provide a non-invasive means for revealing internal organs and tissues of the human body in cross-section to aid in medical diagnosis, surgery, etc. Essentially, an X-ray beam (also including, in certain instances gamma radiation) is passed through the body and the attenuation difference between the transmitted beam and the detected beam is sensed by a detector system, digitized and stored in a computer. The beam is then rotated in one plane to a different angular position and the attenuated beam's energy at that position similarly recorded. The process continues for 360°, at which time the computer images the data recorded to develop a two dimensional picture of a cross-sectional slice taken through the patient which corresponds to the plane in which the X-ray beam was rotated. The X-ray beam is then transversely moved and the process repeated to develop another picture of a cross-sectional slice of the patient. By taking a plurality of such transversely spaced slices and stacking them one on top of the other, a three dimensional transparent view can be constructed by the computer.

The first commercial application of computerized axial tomography (CAT) is attributed to Hounsfield in 1972 and used a pencil beam with a single detector. The beam and detector were simultaneously rotated and then linearly translated to develop an appropriate scan of the organ. This is conventionally referred to as the first generation scanner. To reduce the time required for the scan, the pencil beam ray was replaced by a beam of X-rays orientated in a thin fan-shaped pattern with the attenuated rays in the fan sensed by a plurality of detectors on the opposite side of the body. Various detector arrays and detector-beam movements were subsequently developed in second, third and fourth generation scanners, all of which were directed to increasing the speed of the scan. In all scanners of the first through fourth generation, a three dimensional view of the scanned object was obtained by, first computing an image of a cross-sectional slice and then stacking such slices to construct a three dimensional transparent or translucent image.

There are inherent problems in medical scanners of the first through fourth generation which preclude their use in industrial applications. Conceptually, any system that rotates a beam to obtain several one dimension images which are subsequently combined to produce a cross-sectional "slice" and which then translates the beam to build a plurality of slices requires a scan-compute time which is simply too slow for industrial inspection purposes. Also, any fan beam in reality has a finite width or a depth while the cross-sectional slice is assumed to be a planar line. Accordingly, there are numerous prior art patents relating to detectors, collimators, scatter shields, etc., which have been designed to reduce the beam width and improve image resolution. Finally, in three dimensional imaging, the computer uses various formulae, assumptions and corrections to calculate what the irradiated object looks like in the space between the slices. Where high resolution and accuracy is required, numerous slices must be taken to build an accurate three dimensional image.

In addition to such problems, first through fourth generation scanners cannot accurately image certain moving organs such as the heart. Accordingly, there have been recent developments in the medical field reported in the Robb et al article which utilize a cone beam instead of a fan beam and an area detector in place of the one dimensional detector arrays to provide such a system.

It is known that a cone beam of X-rays can be developed and that such beam can be projected onto a fluoroscopic screen or recorded on photographic film for two dimensional imaging. A number of papers have presented formulae for cone beam back projections which are used to construct the images in a computed tomographic system. Despite the number of papers, the use of cone beams in three dimensional X-ray computed tomographic systems has only been reported as successfully practiced in the medical scanner(s) described in the Robb et al article. In the Mayo Clinic scanner described in Robb's paper, multiple X-ray tubes are placed around a 160° arc of a circular gantry which mechanically rotates about the patient while carrying a diametrically opposed fluorescent screen. The screen records two dimensional shadow data for each of the X-ray cone beam sources which are described as being fourteen in number. The orientation of the object to be scanned is such that the distance from the source of radiation to the object is significantly greater than the distance from the object to the detector so that the transmitted beams in the cone striking the screen can be viewed as parallel beams to permit reconstruction in the manner of a fan beam slice system. Conceptually, the system developed at the Mayo Clinic is sound and represents a significant advance in the medical field permitting heart studies and the like. The geometrics of the system are such that while adjacent cone beams can be formed to uniformly irradiate an object, the attenuated beams in the adjacent or fringe areas will interfere with one another before striking the detector. For this reason, the fluorescent screen is positioned close to the patient. While the interference can be compensated for at the detectors, commercial objects having high mass densities would produce weak fringe signals making it difficult to obtain accurate high resolution signals or increasing the scan time, etc.

In the related nuclear medicine field, Technicare U.S. Pat. No. 4,302,675 discloses an adjustable collimator in combination with a scintillation camera where the pinhole axes in the collimator are movable to record various incident angles of gamma rays emitted from an object to construct a simulated three dimensional image of the object. Also, Hounsfield U.S. Pat. No. 4,322,684 discloses a three dimensional imaging technique utilizing nuclear magnetic resonance where resonance is induced in a plurality of planar slices through an object which is rotated about a first axis and then further rotated about a second axis. The slices are then integrated to obtain a three dimensional view. Neither nuclear medicine application uses X-rays emitted from a point source travelling in straight lines.

B. Industrial Applications

While it can be appreciate that numerous principles of computer tomography are applicable to both medical and industrial applications, there are several requirements for tomographic systems which are unique to industrial systems. Cost considerations require a scanning time which is significantly shorter than what is acceptable in the medical field. In addition, there are many assembly line applications which require three dimensional inspections of fast moving objects. Also, in many instances, industrial applications must produce accurate images capable of very small dimensional inconsistencies. In this sense, industrial tomographic applications based on scan time-image resolution considerations are more severe than medical applications. Finally, in many applications, the size of the specimen presents inherent beam penetration problems which cannot be necessarily solved by changing from soft to hard x-rays or increasing the energy intensity of the source, etc.

Industrial radiography (the recording of the differential absorption of hard radiation such as X-rays, gamma rays, etc. on photographic film to disclose two dimensional images) has long been used to detect internal physical imperfections such as voids, cracks, flaws, segregation, porosities, and inclusions in the finished article of manufacture. Additionally, the use of a fluorescent screen to permit high speed visualization of the X-ray shadow images has also been long utilized. In Green U.S. Pat. No. 3,758,723 a fluorescent screen is utilized in combination with an optic lens, a light intensifier and a vidicon tube (electron beam camera) to record a picture which is snatched and projected onto a television monitor while the article being viewed is indexed to another position for its next two dimensional X-ray picture. In other industrial applications such as discussed in Houston U.S. Pat. No. 4,392,237, Xenon detectors have conventionally been used with collimated pencil X-ray beams which act as flying spot scanners for baggage systems, bottling plants and the like.

The Houston patent expands the pencil beam concept to a fan beam principal in combination with a plurality of detectors (not entirely dissimilar to the second generation systems described above) to detect two dimensional views of objects passing through the fan beam. Despite many statements in the literature to the contrary, industrial inspection techniques which have been successfully commercialized prior to our invention essentially use one dimensional beams projected onto one or two dimensional detectors to record two dimensional pictures of the inspected object.

Within the literature, an article entitled "Practical Cone-Beam Algorithm" published in the *Journal of the Optical Society of America*, (one of the articles incorporated by reference herein) by L. A. Feldkamp et al, reported on a laboratory system consisting of a microfocus x-ray source, a single axis rotational stage and the x-ray image intensifier with associated electronics. The paper demonstrated a convolution back projection algorithm for use in CT image construction using a cone beam. The system discussed in the Feldkamp paper inherently possesses several advantages over conventional CT systems. Principally, the system is conceptually able to compute a three dimensional image upon a single 360° revolution of the irradiated object about one of its axis. Additionally, the problem associated with the "thickness" of the beam in fan cone systems is eliminated by this system. Thus, image resolution is enhanced while the scan-compute time is significantly lessened. The system disclosed in the Feldkamp article has been used in closely controlled laboratory conditions on small parts and is fundamentally sound. However, a number of problems are encountered when the system, in its fundamental concept, is applied to various CT industrial applications where part geometry, size or environment require system modifications to either permit imaging or improve image resolution and/or speed.

SUMMARY OF THE INVENTION

Accordingly, it is a principal object of the present invention to provide an improved, industrial computerized tomographic system which can produce sharp images of industrial objects and the like in a short time.

This object along with other features of the invention is achieved in a computerized tomographic industrial radiation system capable of constructing a three dimensional transparent image of at least a portion of an industrial part or similar object which includes i) a point source generator for generating a non-pulsed, three dimensional cone beam of hard radiation, ii) a collimator associated with the generator for controlling the cone angle and the peripheral configuration of the cone beam, iii) a positioning mechanism for locating the object in the path of the cone beam such that a predetermined volumetric portion of the object is exposed to the three dimensional cone beam of hard radiation, and iv) a two dimensional detector arrangement fixedly aligned with the point source generator and located on the side of the object opposite the object's side exposed to the hard radiation. The detector arrangement is of the type which receives attenuated radiation and converts the radiation through scintillation into a two dimensional shadow image and includes digitizing means for collecting the two dimensional shadow image into an ordered array of digitized numbers such that each digitized number in the array corresponds to the energy level of attenuated beams of radiation at a given location in the array. A computerized arrangement is provided for storing the digitized numbers and imaging two as well as three dimensional transparent image of a predetermined volumetric portion of the irradiated object. The positioning mechanism includes means for positioning the object in a three dimensional relationship relative to the source and means for intermittently rotating the object relative to the point source and the detector arrangement about only one axis of the object through a predetermined angular movement. Importantly, the single axis of rotation is centered about the predetermined volumetric portion of the object to be imaged and not necessarily about the object's geometric center to permit high image resolution of a defined portion of the object through no more than one revolution of the object.

In accordance with a more specific feature of the invention, the time for completing the scan is reduced while the image resolution is enhanced by rotating the irradiated object off center from its geometric center such that the distance from the object's center of rotation to the detector screen is a minimum when the mass volume of the object penetrated by the hard radiation is at a maximum. This normalizes the range of radiation sensed by the detector arrangement during rotation to permit image enhancement while also minimizing the time required to digitally sense the shadow image developed in the scintillation screen.

In accordance with still yet another more specific aspect of the invention, the rotation of the irradiated object is along an elliptical or alternatively an eccentric, arcuate path as contrasted to a circular path such that the greatest volumetric mass portion or density of the object penetrated by the radiation is positioned closest to the detector arrangement to minimize adverse magnification effects on the scintillation screen at the outermost boundaries of the radiation cone beam.

In accordance with another aspect of the invention when the object's size is such that the object has at least two cross-sectional areas in any two orthogonal planes which is greater than the area of the detector arrangement, the positioning mechanism positions the object so that the cone beam initially passes through a first portion of the peripheral surface of the object and the rotating means is effective to rotate the workpiece about a first axis which is offset from the center of the object through one revolution. Thereafter, the positioning means translates the object such that the cone beam passes through a second portion of the peripheral surface whereat the rotating means is effective to rotate the object through only one revolution about a second axis. The imaging means is effective to construct a three dimensional image of the entire object. Preferably, the first and second axis of rotation are coordinated relative to the mass volume density of the object to position the largest mass volume closest to the detector system to minimize scan time and enhance image resolution. Further, it is possible to obtain a three dimensional image of the object by not sampling the object through a predetermined angle of rotation and positioning the maximum mass density of the irradiated object to pass through the predetermined angle to reduce the scan-compute time.

In accordance with another aspect of the invention, the positioning means initially locates the object at a position between the generator source and the detector mechanism such that the initial shadow image produced by the detector mechanism represents substantially the complete cross-section of the object in a two dimensional spatial relationship. The imaging means is effective to construct a two dimensional cross-sectional image, i.e. a digitized radiograph, corresponding to the shadow image and the operator is provided with a mechanism for manually selecting a portion of the cross-sectional image for volumetric viewing. The positioning means is responsive to the actuation of the operator mechanism to move the object closer to the generator source and thus increase the magnification and enhance the image resolution of the detector arrangement. The imaging means constructs a volume image encompassing only the selected through one complete revolution to permit greater resolution of small object details.

In accordance with a more specific feature of the invention, the system optimizes the maximum object size for a given scintillation screen which can be three dimensionally imaged, per se, as well as in combination with the pan and zoom feature discussed above. Definitionally, the system is orientated along x, y and z axes perpendicular to one another with orthogonal planes passing through any two of the three axes. The scintillation device is situated in a plane passing through the y-z axis and the x axis intersects the y-z plane at a center point. The generator's point source is situated on the x axis and extends a distance to the center of rotation of the object equal to a distance-SRAD and the center of the scintillation screen extends a distance in the opposite direction from the object's center of rotation equal to a distance DRAD. The object has a maximum y distance extending along the y axis and a maximum z distance extending along the z axis. The positioning means is operable in combination with the collimator associated with the point source to position the object along the x axis between the point source and the scintillation screen such that the object's maximum y distance when divided by SRAD does not exceed the scintillation screen's y dimension when divided by DRAD added to SRAD and the object's maximum z distance when divided by SRAD does not exceed the scintillation screen's z dimension when divided by DRAD added to SRAD so that the entire object can be three dimensionally imaged upon only one complete rotation of the object.

In accordance with still yet another specific feature of the invention, the resolution capability of the system disclosed is optimized when the zoom feature of the invention is employed to establish an image which is clear enough to distinguish voxels of "R" size based upon the finite diameter of the point source, "FSS" (focal spot size), and the actual finite size of individual detectors, "DS" (detector size), assuming a satisfactory detector matrix size and a sufficient number of two dimensional slices. The main processor, utilizing the encoder information from the system drives, initially calculates, by means of similar triangle ratios, the distance SRAD assuming a point source at the detector screen and a focal spot of diameter FSS and then calculates the distance SRAD assuring a point source at the generator and a diametrical detector size of DS and chooses the longest SRAD distance. Should the voxel size then established be too large for the industrial application, the optimally spacing between the point source and detector screen along the x—x axis may be varied by iterative calculations of the processor until the desired resolution is obtained or the system's dimensional limits are met.

In accordance with another specific feature of the invention, the scan-compute time and image resolution capability is increased by utilizing a priori information to dynamically vary the flux or intensity of the hard radiation emitted from the source and/or dynamically vary the integration of the flux or attenuated radiation recorded by the detector array. The a priori information is established by an initial scan of the object which correlates the drive encoders to the various mass densities of the object taken at each angular increment while the object is rotated about its y—y axis. The intensity of the generator is then varied during the object's rotation to produce a more homogeneous light photon range between two dimensional slices throughout the scan to permit more sensitive detector readings over an overall shorter scan time. The digitized detector readings are subsequently modified to account for the variation in radiation intensity. Alternatively, the detectors are conventional current integrated devices, and in accordance with known noise signal considerations must integrate light photons emitted from the scintillation screen correlated to large object mass densities over a longer period of time than that for small mass densities. The a priori information is utilized to vary the integration time in a fashion somewhat similar to that used in the dynamic flux variations of the generator beam.

In accordance with a still more specific object of the invention, the irradiated object need not be stopped in its rotational motion while two dimensional image data is being taken and the number of images taken can be varied in number to permit three dimensional inspection of at least selected volumetric portions of industrial objects moving at fast linear speeds indicative of an assembly line environment.

It is thus an object of the invention to provide an industrial CT system which permits a three dimensional transparent image of a large object to be taken in a short time.

It is another object of the invention to provide an industrial CT system which permits sharp resolution of three dimensional images of irregularly shaped objects.

It is another object of the invention to provide an industrial CT system which permits sharp resolution of large, irregularly shaped objects in a short time.

It is still yet another object of the invention to provide an industrial CT system which not only can take three dimensional transparent views of the object but also two dimensional views through any plane of the object.

It is still yet another object of the invention to provide an industrial CT system which provides an operator controlled zoom feature permitting three dimensional viewing of a selected volumetric portion of an irradiated object.

In accordance with the immediately preceding object, it is still a further object of the invention to provide a CT system which can image small voxels of the irradiated object.

Yet another object of the invention is to provide an industrial CT system which is quicker in scan time than that of the prior art.

Still a further object of the invention is to provide an industrial CT system which produces higher image resolutions than that previously afforded in such systems.

Still another object of the invention resides in an improved industrial CT system resulting from the combination of some or all of the features enumerated above.

Still a further object of the invention is to provide a simple and economical CT system and/or a functionally improved CT system.

These and other objects of the invention will become apparent to those skilled in the art upon reading and understanding the detailed description of the preferred embodiments of the invention set forth below.

BRIEF DESCRIPTION OF THE DRAWINGS

The invention may take physical form in certain parts and arrangement of parts, preferred embodiments of which will be described in detail and illustrated in the accompanying drawings which form a part hereof and wherein:

FIG. 7 is a schematic pictorial representation of the hardware associated with the system.

FIGS. 8a, 8b and 8c schematically illustrate plan views of the rotation of an object within the scan enclosure;

FIGS. 9a and 9b illustrate various paths of irradiated object rotation within the scan enclosure;

DETAILED DESCRIPTION OF THE PREFERRED EMBODIMENT

Figure 1:
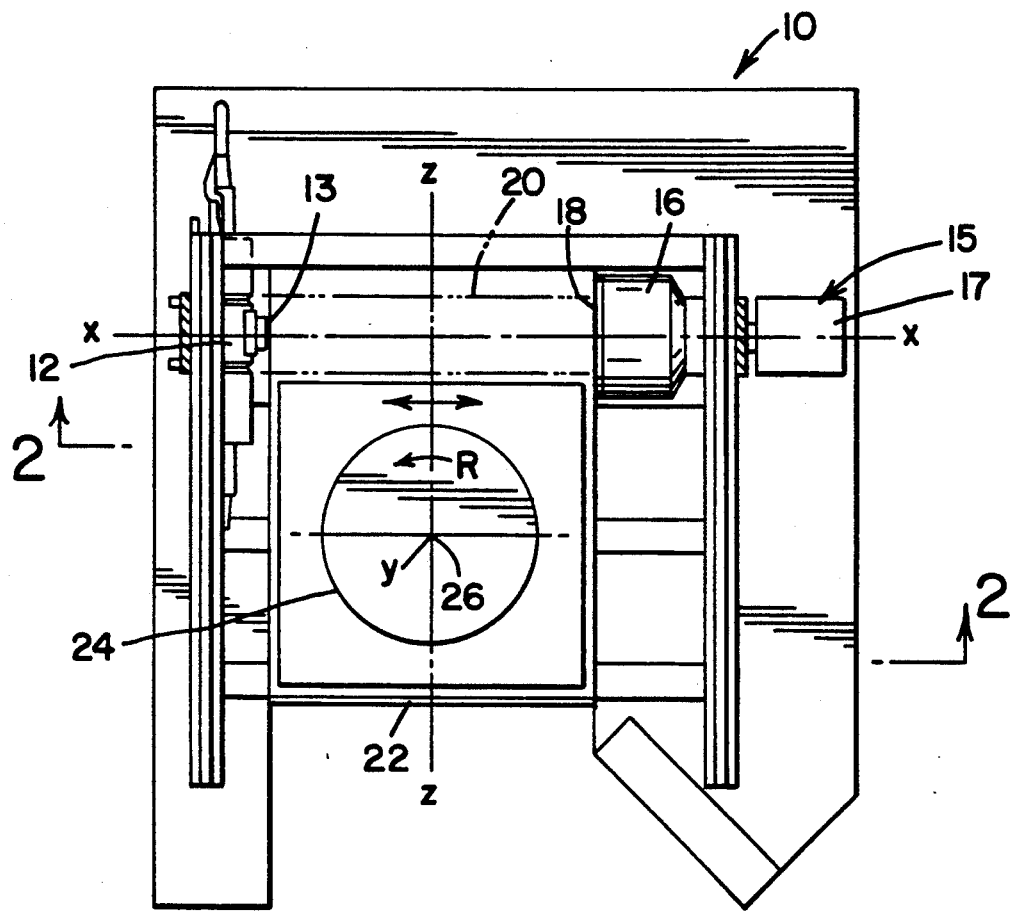
FIG. 1 is a schematic plan view of a scan enclosure.
Figure 2:
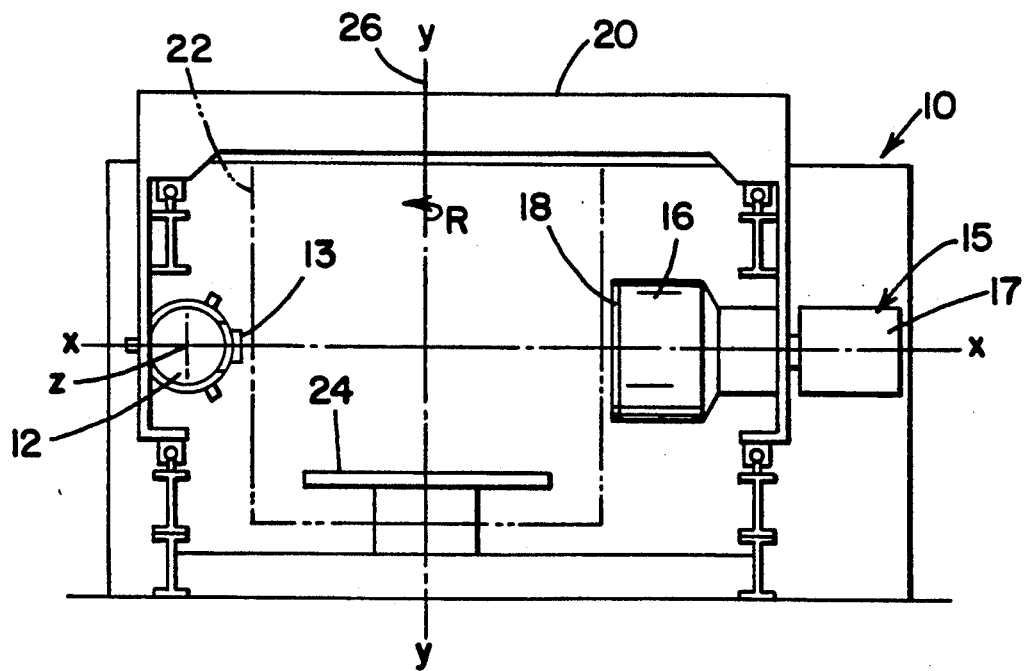
FIG. 2 is a schematic side elevation view of the scan enclosure of FIG. 1.
Figure 3:
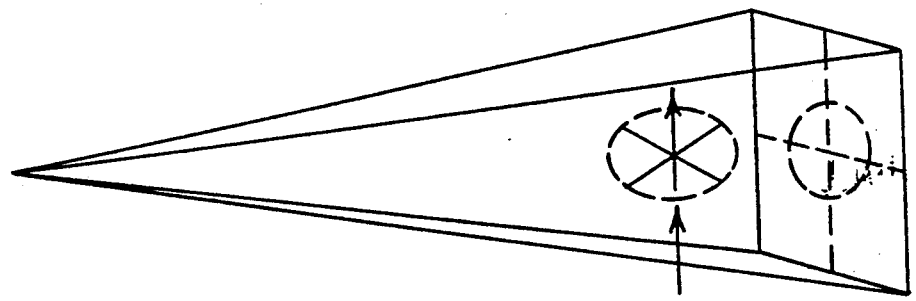
FIGS. 3, 4 and 5 illustrate pictorially the steps in a three dimensional reconstruction process employed in the invention.

Referring now to the drawings wherein the showings are for the purpose of illustrating preferred embodiments of the invention only and not for the purpose of limiting the same, there is shown in FIGS. 1 and 2 a scan enclosure 10 which is completely lined with lead to prevent radiation leakage therefrom. Within scan enclosure 10 is an x-ray generator source 12. X-ray generator 12 is conventional and generates from a point source a cone shaped beam of hard radiation. A suitable x-ray generator is model number MN 451 produced by Philips GmbH which has a rated power source of 450 kv although, depending on the application and size, generators with a power source as low as 125 kv can be used. While generator 12 is conventionally defined as a point source generator, in practice the x-ray source has a finite focal spot which, for the application discussed in this specification, typically range between 1.5 mm and 4 mm. Other X-ray sources have different ranges. Attached to x-ray generator 12 is a collimator 13 which shapes the peripheral pattern of the cone beam boundary and controls the cone angle of the cone beam. Collimator 13 is conventional and will not be described in further detail and is to be distinguished from cone shaping mechanisms which selectively control the intensities of x-ray beams emitted from generator 12. X-ray generator 12 is generally adjacent one side of scan enclosure 10 while an x-ray detector means 15 is situated generally adjacent the opposite side of scan enclosure 10. Detector means 15 can comprise any one of several arrangements conventional in the art. In the embodiment disclosed in FIGS. 1 and 2, detector means 15 includes an image intensifier tube 16 and a video camera 17. Reference may be had to the vidicon-lens intensifier arrangement designated by numerals 20–31 in Green U.S. Pat. No. 3,758,723 (incorporated by reference herein) for a description of a suitable intensifier tube 16-video camera 17 arrangement which can be used in the present invention. As is conventionally known, intensifier tube 16 converts the attenuated beam's x-ray energy to light through scintillation and a two dimensional fluorescent screen or crystal is used to develop a "shadow image" of the irradiated part. Video camera 17 is coupled to image intensifier tube 16 by optics, either lens or fiber, and scans the shadow image raster and converts the light energy to analog data. Optionally, a scatter rejection grid 18 can be inserted ahead of the scintillation screen in intensifier tube 16. Scatter rejection grid 18 is a two dimensional array of slits and/or pinholes, each of which is focused on the focal spot of x-ray generator 12 to permit only x-rays that are transmitted along a straight line from x-ray generator 12 to be transmitted to detector means 15.

X-ray generator 12 and detector means 15 are fixed to one another by means of a yoke or gantry 20. Gantry 20 is provided with an appropriate, conventional drive mechanism to permit simultaneous movement of x-ray generator 12 and detector means 15 in the y and z directions. For reference purposes, the x—x, y—y and z—z axis will have that orientation shown in FIGS. 1 and 2 and planar surfaces passing through any two different axes are, by definition, orthogonal to one another. With the axes definition thus established, it is to be noted that the focal spot of x-ray generator 12 lies on the x—x axis which intersects the center of intensifier tube 16. Optionally, the distance along the x—x axis between x-ray generator 12 and detector means 15 can be varied by an x-drive mechanism not shown, and if used in the system this is the only relative movement permitted between x-ray generator 12 and detector means 15. (This could be accomplished by constructing gantry 20 as two L shaped members slotted in the x—x direction.) A door 22 is provided to gain access to the interior of scan enclosure 10 for loading and unloading objects to be inspected. A turntable 24 is positioned between x-ray generator 12 and detector means 15. A drive, not shown, is provided for rotating turntable 24. Also, a drive, not shown, is provided for moving turntable 24 in the x—x direction. It should be appreciated that because the system is concerned with relative positioning, drives could be provided for turntable 24 to move in the y—y and z—z direction and, if so provided, gantry 20 would not be required to effect movement of generator 12 and detector means 15 in the y—y and z—z direction. An encoder, not shown, is provided for each of the drive mechanisms.

Referring now to FIG. 7, an object 25 to be irradiated is placed on turntable 24 and collimator 13 is adjusted so that the radiation's cone beam angle "A" is just sufficient to project over the outer peripheral surfaces of object 25 in the y—y and z—z direction. After the transmitting beams of radiation impact object 25, the attenuated beams of radiation strike what is defined herein as the two dimensional scintillation screen 27. "Scintillation screen" 27 as used herein including the claims hereof means either a fluoroscopic screen or a two dimensional flat scintillation crystal. A suitable scintillation crystal would be cesium iodide doped with thallium and a suitable fluoroscopic screen may, for example, consist of gadolinium oxysulfide or zinc cadmiumsulide. As well known in the art, scintillation screen 27 simply converts the energy of the attenuated x-ray beams striking screen 27 into light photons having a correlatable energy, (i.e. wavelength, color) and when all the transmitted beams of radiation striking scintillation screen 27 are viewed, a two dimensional shadow image 28 is observed.

Light photons from scintillation screen 27 are detected by a detector arrangement 29. As discussed with reference to the embodiment shown in FIGS. 1 and 2, detector arrangement 29 could comprise a vidicon camera or a like camera such as shown in Green U.S. Pat. No. 3,758,723 with or without a fiber optic light intensifier and with or without a lens focusing and/or magnification system interposed between scintillation screen 27 and detector arrangement 29. As the shadow image raster is scanned by the vidicon camera an analog output is serially recorded and subsequently digitized. In this manner, a digital radiograph (a cross-sectional view of object 25 as orientated in FIG. 7 corresponding to the shadow image) can be reconstructed. Detector arrangement 29 could alternatively comprise an array of multi-channel individual detectors. Various photosensitive devices suitable for use in such an array are noted in Hounsfield U.S. Pat. No. 3,881,110, incorporated by reference herein. Alternatively, an area CCD device (charge coupled device) such as those identified by Motorola catalog number listed in Goldman U.S. Pat. No. 4,298,800 (incorporated by reference) can be utilized. Conceptually, each individual detector is located at a precise position in an ordered array or matrix shown extending in a y-z plane and each detector generates an analog signal (usually current) indicative of the energy of the light photons striking the detector which in turn is correlated to the energy of the attenuated x-ray beam's energy at that particular point. The analog signals are serially collected and digitized at which time each signal represents a pixel. Typically the arrays have 512 by 512 individual channel detectors and in some instances 1024 by 1280 detectors for sharp image viewing.

Figure 4:
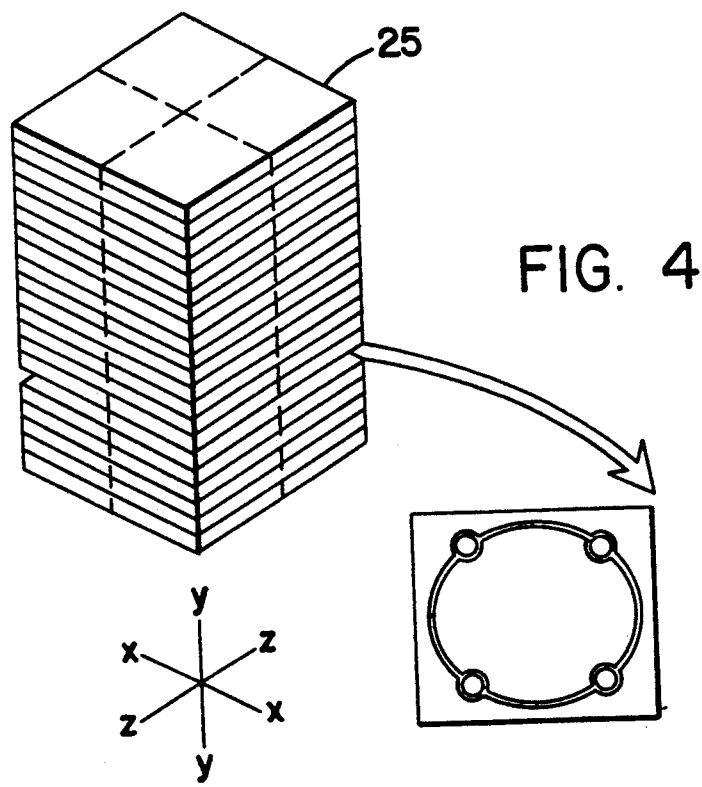
Figure 5:
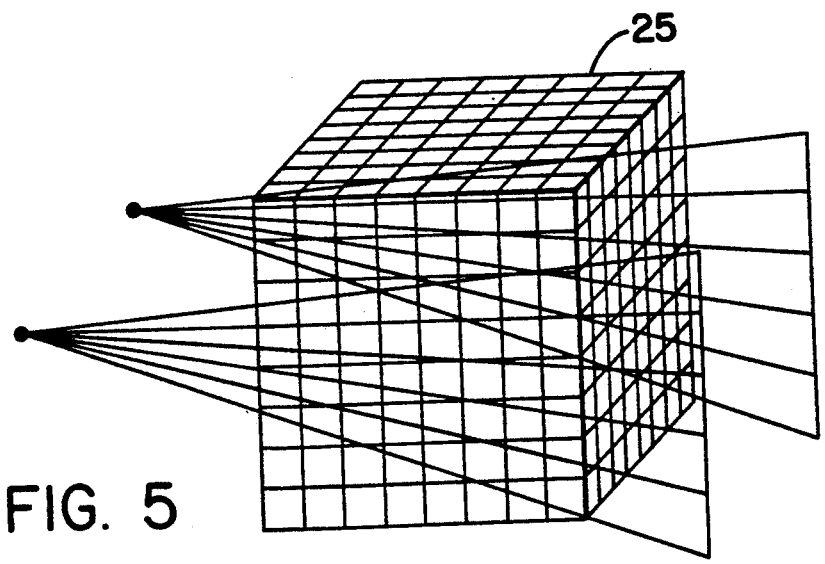

Referring now to FIGS. 3, 4, 5 and 7, preferably object 25 is rotated about a central axis 26 for a predetermined angle, stopped and detector means 15 actuated to record detector 29 readings. During this scan, the detectors record sufficient data so that a two dimensional, digitized radiograph of the cross-section of the object or field-of-view can be constructed. Object 25 is then rotated through another predetermined angle and a second field-of-view recorded and the process is usually continued until the object has rotated through a complete revolution of 360°. Typically 720 field-of-views are recorded in one revolution in about 120 seconds. This is a very rapid rate and, in contrast to medical applications, generator 12 is not pulsed during the scan even though cone shaping mechanisms may be employed to vary the intensity of beams or beam portions within the cone. Thus, each detector in effect records a "pencil" beam of attenuated radiation and this has occurred 720 times by the time the rotation is completed. Each detector thus records x, y, z data correlated to each angular position of object 25 and all of the data is stored. Thus, each detector has recorded in one rotation information equal to that recorded in one complete rotation of a first generation medical scanner and that data for that detector can be used to generate one cross-sectional slice of object 25. Similarly, one row of detectors (y or z axis) is equivalent to the fan beam detector arrangement of the second through fourth generation medical scanners. Thus, the system gathers information in one revolution equivalent to that obtained by y (or z) revolutions of second through fourth generation medical scanners. The data for each detector can then be utilized to construct computerized two dimensional slices (typically 512 or 256 slices) of object 25 shown as cross-sectional planes cutting through the object as shown in FIG. 4 or voxels as shown in FIG. 5 similar to that which is now directly recorded with fan beam CT scanners and this data can then be utilized to construct three dimensional, transparent images using conventional, computer solved, algorithms. In addition, two dimensional images can be constructed through any inclined or oblique plane passing through object 25. There are, however, some fundamental differences in the data obtained by the detectors in the present system when compared to that of the fan beam systems. For example, only the radiation beams falling on the x—x axis correspond to the prior art fan beam arrangements. The other rays are inclined and reference may be had to L. A. Feldkamp's article (incorporated by reference herein) for an appropriate convoluted back projection algorithm which accounts for such inclination and which can be used in the system of the present invention. Another difference is that imaging of off-center voxels result in a magnification of the voxel detected by scintillation screen 27. While it is easy to mathematically account for the magnification, there are difficulties associated therewith in an industrial setting which the system of the present invention overcomes.

Figure 6:
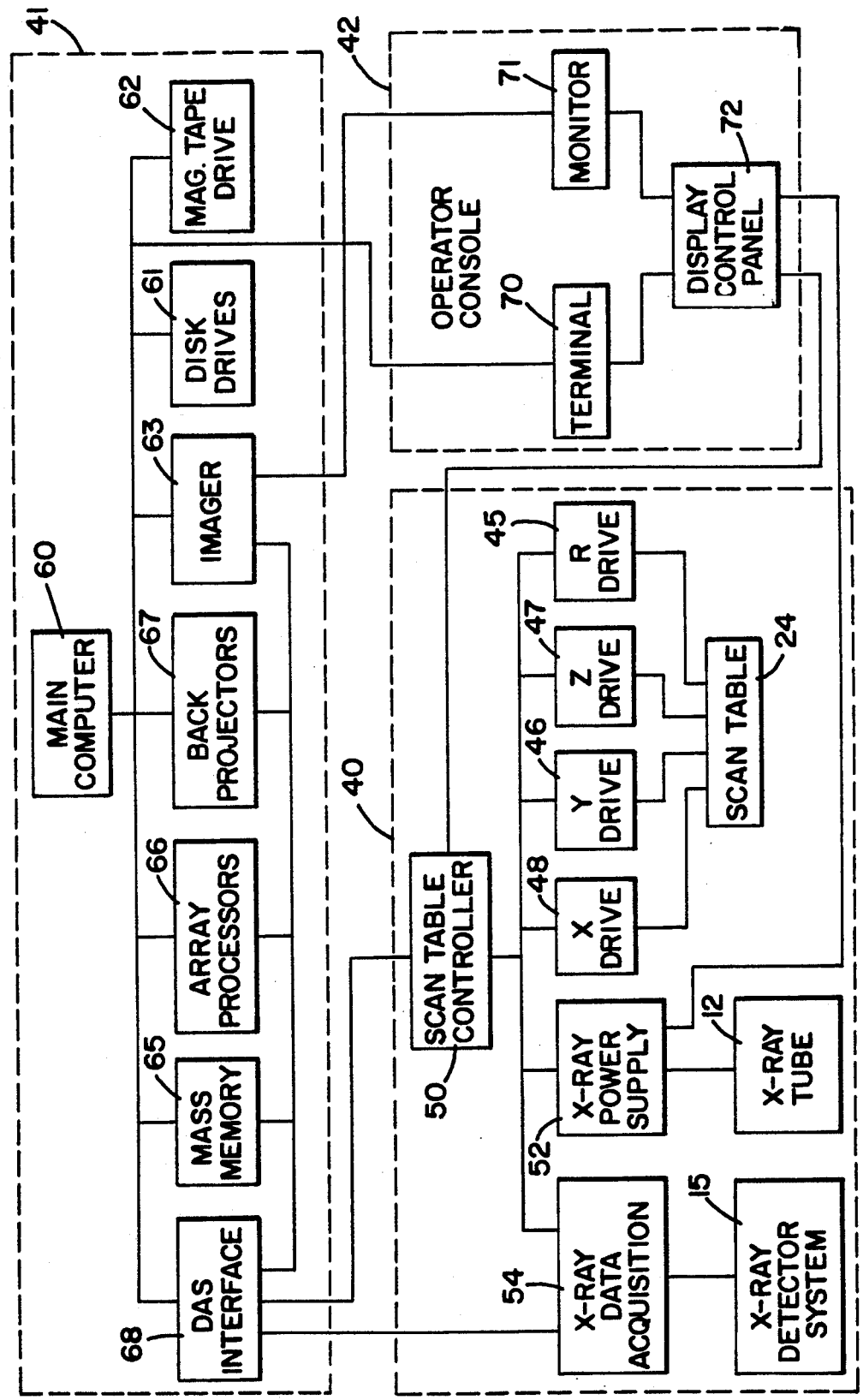
FIG. 6 schematically illustrates the various control functions associated with the scan enclosure.

Referring now to FIG. 6, the imaging system of the present invention includes three separate systems indicated by dash lines in the drawing. The systems include a data acquisition system 40, an imaging processor system 41 and an operator console 42. Each system 40, 41, 42 is interconnected with one another.

Data acquisition system 40 includes, as described with reference to scan enclosure 10 of FIGS. 1 and 2, x-ray tube 12, x-ray detector system 15 and in the sense that scan enclosure 10 is relevant to the drive positioning object 25 between x-ray tube 12 and x-ray detector system 15 a scan table designated as numeral 24 in FIG. 6. In this sense, scan table 24 includes an R drive 45 for accurately rotating object 25 through timed angular increments, a Y drive 46 and a Z drive 47 accurately positioning x-ray tube 12 and x-ray detector system 15 in the y—y and z—z direction, and an X drive 48 for accurately positioning object 25 in the x—x direction between x-ray tube 12 and x-ray detector means 15. Optionally, X drive 48 could also include a drive for varying the spacing between detector means 15 and x-ray source 12. Each of the drive mechanisms 45–48 includes conventional drive motors, drive mechanics, drive electronics and an encoder associated with its respective drive position to indicate the exact position of the system component controlled by the drive. Also, each drive has an interface to a scan table digital controller 50. Scan table digital controller not only controls drives 45–48 but also synchronizes x-ray controls during the scan process. Commands are sent to and from the scan table controller 50 from image processor 41 and operator console 42 to initiate the scan process as well as to indicate the particular scan protocol. As noted, scan enclosure digital controller 50 controls the intensity of the beams emitted from x-ray tube 12 through x-ray power supply 52 and also included in the power supply control 52 is the arrangement for varying the intensity of the x-ray beams within the cone beam should the optional dynamic flux variation concept be utilized. Scan table digital controller 50 also controls the x-ray data acquisition and control electronics ("XDAC") 54. XDAC 54 samples the data from detector system 15 as well as controlling when to sample the data as synchronized by the scan enclosure controller 50. Sample data from XDAC 54 is then sent to image processor 41 for reconstruction. XDAC 54 includes a data digitizer which converts analog data from x-ray detector system into digital data and stores the data into a high speed digital memory, i.e. a buffer. The data digitizer is interfaced to image processor 41. XDAC 54 also includes a data digitizer controller which takes inputs from scan table digital controller 50 and instructs the data digitizer, usually as a function of position of object 25, when to take its sample.

Image processor 41 receives the data from data acquisition system 40 and processes the data into the desired three dimensional density volume as well as processing other images and performing data analysis functions. The major hardware sections of image processor 41 include a main computer or main processor 60 which preferably is a Micro Vax II configured with the proper peripherals to control all functions of the CT system. Main processor 60 is coupled to several major subsystems within image processor 41 as well as to the data acquisition system and the operator console 42. The subsystems in image processor 41 include a disk controller and disk drives 61 which are used for program software and data storage. A mag tape controller and mag tape drive 62 is used to transfer software and data to and from the CT system. An imager 63 is used to display processed images on a monitor in the operator's console 42. Imager 63 has its own dedicated memory, look up tables and digital video processor to perform imaging processing functions and image manipulation functions. Functions which the imager can perform are window and center functions, pan and zoom functions, image manipulation functions, image metric functions, image processing functions, alpha numeric generation, cursor generation, high speed load functions, graphic functions and color presentations Systems which are used to refine collected data sent to imager 63 include a mass memory 65 which stores data collected from data acquisition system 40 temporarily while scanning of the object 25 is in progress. Also, mass memory 65 is used to allow rapid access to raw data and image data for reconstruction of the images and array processors 66 are provided to process the large amount of data from data acquisition system 40 into images. Rapid floating point operations can be performed by array processors 66 which are interfaced to mass memory 65 as well as main processor 60. Back projection hardware 67 is used to perform the back projection for x-ray reconstruction and is connected to both array processors 66 and mass memory 65 to allow rapid reconstruction of the image. A suitable algorithm utilized in the back projector 67 to construct three dimensional images is set forth in the Feldkamp article cited above. Finally, a data acquisition system interface 68 allows rapid transfer of data collected from data acquisition system 40 to image processor 41. Also, data acquisition system interface 68 transfers bi-directionally the control of status commands between data acquisition system 40 and image processor 41.

Hardware for operator console 42 includes an operator terminal and keyboard 70 connected to image processor 41, image viewing monitor 71 connected to imager 63 and an operator scan control and display control panel 72 connected to terminal 70 and monitor 71 and also to scan table controller 50 and x-ray power supply 52. Operator terminal and keyboard 70 preferably includes a Micro Vax II GPX 19 inch work station monitor, keyboard and mouse integrated into the console structure and preferably is menu driven by the mouse. The menus contain the particular scan protocol and each protocol contains all the necessary a priori information needed to operate the system automatically. During operation, terminal 70 will display critical scan data information on monitor 71 which will have window, centering and cursor display functions for use with the reconstructed object picture. Control panel 72 provides for direct operator control for certain specific functions such as start scan control, abort scan control, emergency stop, x-ray enable, x-ray disable, hold scan, resume scan, window and center knobs, track ball for cursor and plain selectors, knobs for size, shape, image intensity, etc.

Figure 10A:
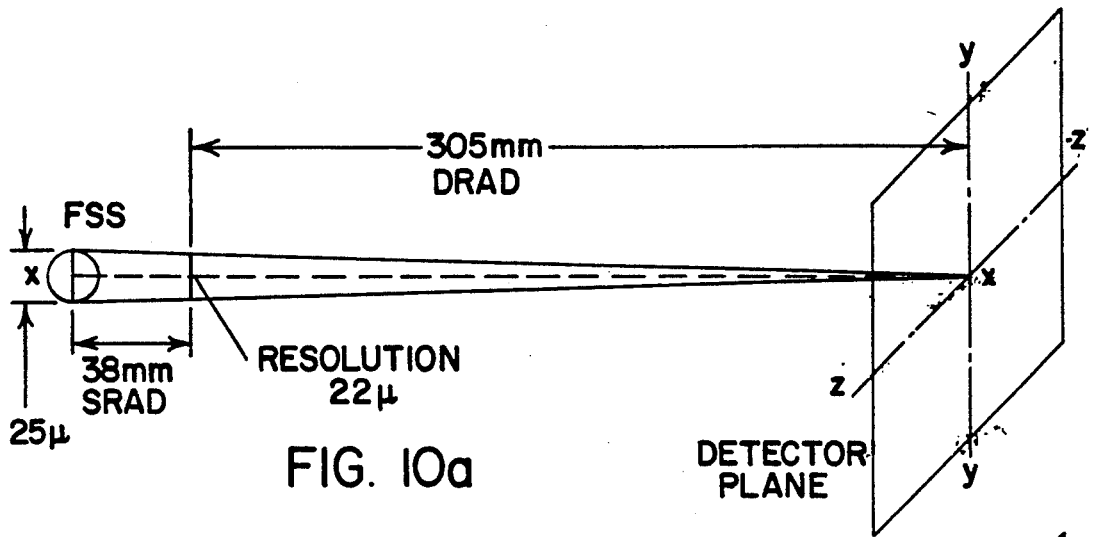
FIGS. 10a, 10b and 10c illustrate schematically the positioning of an object within the scan enclosure.

The general system has been explained with reference to various components and the components, per se, are conventional. The manner in which the components are combined and operated, however, render the system particularly suitable for industrial CT applications. Reference may be had to FIGS. 10 and 11 for discussion of what may be described as a pan and zoom feature of the invention. Generally speaking, for a fixed "x" dimension between the focal spot of x-ray generator 12 and scintillation screen 27 of detector means 15, collimator 13 is constructed to form a right angle cone of x-ray beams having a cone angle A such that the cone beam will strike the entire area of scintillation screen 27. If scintillation screen 27 is rectangular in area, then collimator 13 will form the cone beam as a rectangular beam which will expand to encompass the y-z area of scintillation screen 27. Object 25 is then placed on turntable 24 and the turntable's X drive actuated to position object 25 within the cone beam at a distance from the focal source generator 12 such that a two dimensional digitized radiograph of the entire object 25 can be viewed in monitor 71. The operator can now, by means of a control such as a track ball 75 on control panel 72, select a specific volume of object 25 which can be viewed in three dimensional detail. The operator positions the area to be volume scanned between two cursor lines 77, 78 and pulls down and actuates the appropriate menu on terminal 70. When this is done, the Y and Z drives are actuated to focus the selected volumetric portion of object 25 to be imaged which will be centered with respect to generator 12 and scintillation screen 27 while the X drive on turntable 24 is actuated to move object 25 closer to generator 12 such that the portion desired to be scanned substantially encompasses the y-z area of scintillation screen 27. In this manner, the three dimensional image can be enhanced to detect very fine discontinuities, porosities, defects, inclusions, etc. in the critical mass portions of the object to be scanned.

Figure 10B:
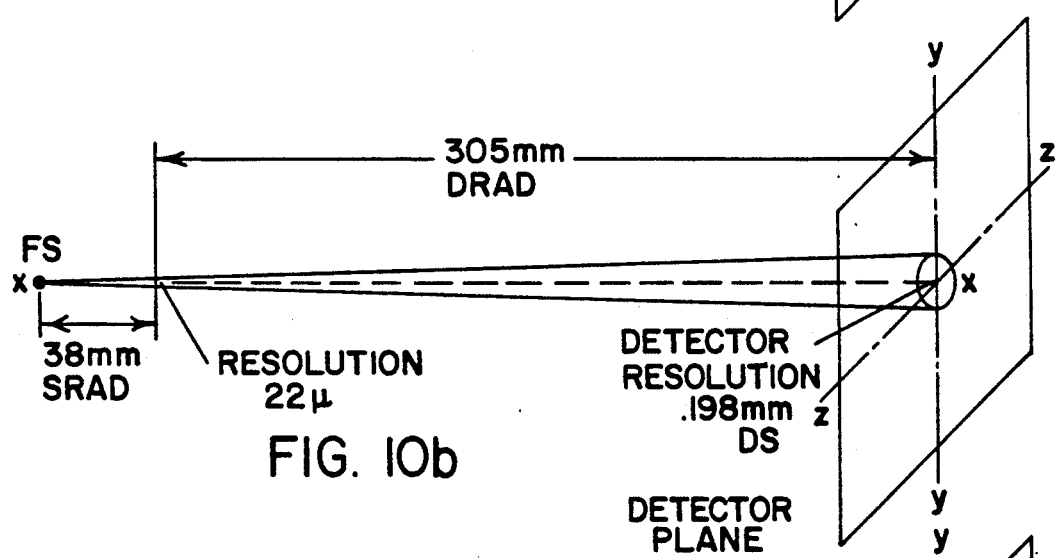
Figure 11:
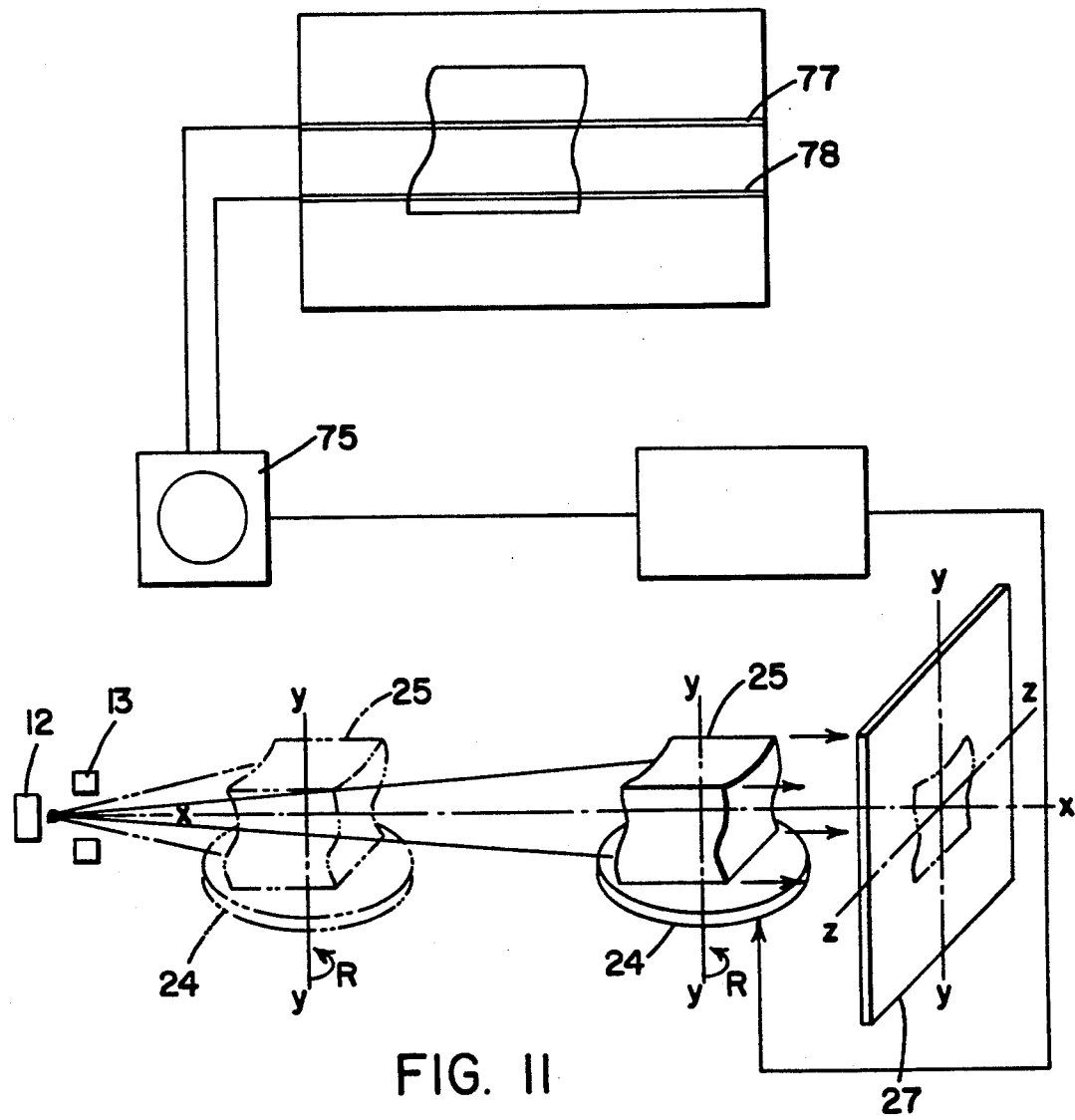
FIG. 11 illustrates schematically the zoom feature of the system.

The actual image resolution of the CT system is a function of the focal spot size of the generator ("FSS" in FIG. 10a), the detector resolution (i.e. the diametrical size of the detectors in the channeled array, "DS" in FIG. 10b), the detector sampling (i.e. the number of slices), the distance from the focal spot source to the center of rotation of the object (defined as "SRAD" in FIGS. 10a, b and c), the distance from the detector to the center of rotation of the object (defined as "DRAD" in FIGS. 10a, b and c) and the final image matrix size (pixel array).

Figure 10C:
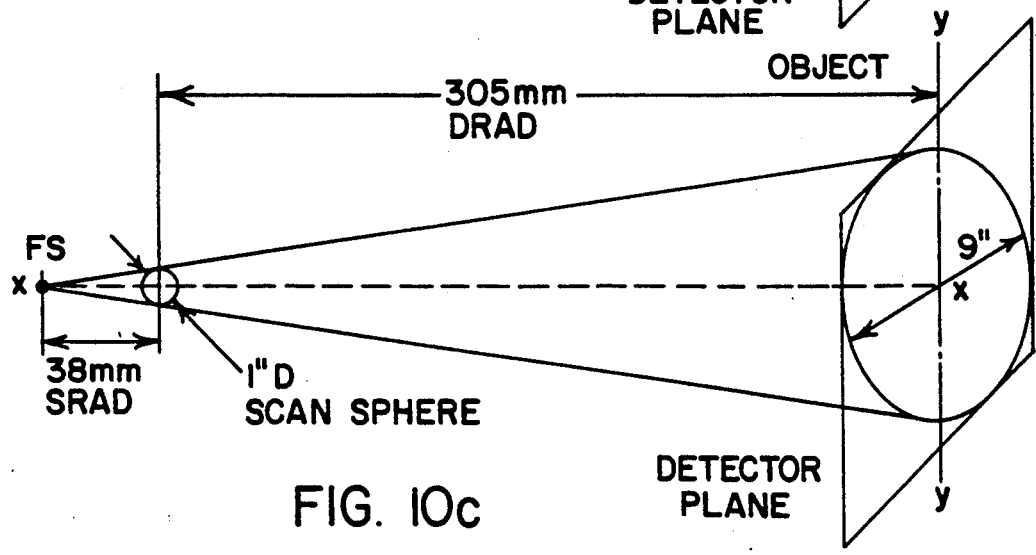

In practice, the actual focal spot size, FSS, is known and the size of an individual detector DS in detector means 15 is also known and the size of the matrix of the screen is also known. The distances SRAD and DRAD are not known. Accordingly, FIGS. 10a through 10c illustrate the various system relationships utilized to establish a zoom position necessary to resolve a 22 um contrast object. First, as shown in FIG. 10a, the limiting resolution due to the actual focal spot size, FSS, is determined by constructing a triangle with its apex at the detector and its base at the focal spot, FSS, and the same size as the focal spot. This assumes that there is an infinitesimal small detector with a finite focal spot in the detector plane. Next, at a distance DRAD from the infinitesimal detector a second base line, i.e. the resolution, is drawn through the triangle. By similar triangles, the ratio of the focal spot base line to the DRAD base line (resolution size) is the same as the ratio of SRAD plus DRAD is to DRAD. The formula then for the resolution based on the focal spot size=(FSS*DRAD/(SRAD+DRAD). In FIG. 10a, assuming the actual focal spot of generator 12 is 25 um, then for a resolution of 22 um, the SRAD and DRAD distances are shown to be 38 mm and 305 mm respectively.

Next, the limiting resolution due to the detector size is considered as shown in FIG. 10b. This is done by constructing a triangle with its apex at the point focal spot FS of the generator and its base at the detector in the detector plane and equal to the same size as an individual detector. This assumes that there is an infinitesimally small focal spot on the generator with a finite sized detector. At a distance SRAD from the infinitesimal focal spot, FS, another base line is drawn through the triangle. By similar triangles, the ratio of the detector base line, DS, to the SRAD base line, i.e. the resolution, is the same as the ratio of SRAD plus DRAD is to SRAD. The formula for the limiting resolution due to the point detector size=(DS*SRAD)/(SRAD+DRAD). In the example given for this calculation in FIG. 10b, if the size of the individual detector is approximately 1.98 mm in diameter, a detector resolution size of 22 um will occur at a DRAD distance of 305 mm and an SRAD distance of 38 mm. The fact that the dimensions for DRAD and SRAD are equal for FIGS. 10a and 10b is a coincidence. In practice, the relation will be limited by either FIG. 10a or 10b and the calculation establishing the longest SRAD will be used.

FIG. 10c is basically the same figure as shown in FIG. 11 and shows that for a detector arrangement 29 having a matrix size which computes out to an area encompassing a circle having an approximate diameter of 9 inches and a cone angle of "A", a sphere or a scan cylinder of approximately 1 inch in diameter at the SRAD and DRAD distances given can be viewed in three dimensions with a 22 um resolution assuming a sufficient number a slices are taken. The 22 um is equivalent to the voxel size as graphically demonstrated in FIG. 5. Thus, it is a specific feature of the invention that for any given CT system, the main processor 60, for any given voxel size, will instruct scan table controller 50 to control X drive 48 for turntable 24 as well as R drive 45 and Y and Z drives 46, 47 to produce the desired resolution of a volumetric portion of object 25 or alternatively, for a desired volumetric portion as established by cursor lines 77 and 78 the minimum voxel size of the system will be computed. Should it occur that for a desired volumetric viewing portion of object 25, the resolution is not small or sharp enough (or for the desired resolution, the volumetric view is smaller than desired), it is possible, as noted above, to modify gantry 20 to vary the total x—x spacing (SRAD plus DRAD) and collimator's 13 cone angle "A" accordingly. (The collimator, in its simple form, is simply a circular hole in a block which can be positionally located relative to the x-ray source to vary the cone angle "A"). Main processor 60 can then iteratively calculate the optimal DRAD and SRAD distances established by FIGS. 10a and 10c to produce the desired resolution and scan cylinder size. Also, in this connection, since the intensity of the hard radiation varies as a power function relative to the distance travelled by the radiation, the smallest overall path distance of the X-rays is maintained, i.e. SRAD plus DRAD relative to the desired resolution and the volumetric portion of the object to be imaged.

Referring now to FIGS. 8a through 8c, whenever the size of object 25 is such that the cross-sectional area of any two orthogonal planes through the object exceeds the cross-sectional area of scintillation screen 27, three dimensional imaging of the object proceeds in at least two steps. For example, the object 25 is rotated about two axes 81, 82 in the y—y direction which are offset from the geometric center 80 of object 25. Specifically, object 25 is initially rotated through one complete revolution on axis 81 and the appropriate drives actuated to reposition the object whereupon it is rotated upon its second offset axis 82 through one complete revolution. Image processor 41 constructs a three dimensional object image from the data obtained in both rotations. As best indicated in FIG. 8b, in any multi-step, off center scan procedure, there will be an object position during the rotation where the radiation must, in effect, be transmitted through the object where its thickness or mass volume density is some multiple of the object when compared to that thickness or density dimension of the object at the start of the initial off center scan. At this "multiple" mass volume density, the x-ray attenuated beams energy is significantly less than the energy level of x-ray beams passing through less dense portions of the object during the off center rotation. When this occurs and as is well known in the art, the scattering and absorption effects attributed to the density reduce the number of x-ray photons which strike and are absorbed in scintillation screen 27 when compared to that passing through less dense portions of the object. Accordingly, the bundle of light photons emitted from screen 27 which are optically coupled to detectors 29 is reduced. This increases the time required for the detector to generate an adequate image signal whether the detector be of the counting type or whether the detector be of the current integration type which measures the total energy over a time period long enough to reduce signal noise. This problem becomes more severe for those x-ray beams emanating from the point source which do not impact at the center of scintillation screen 27. The beams at the outer portion of the cone beam array magnify the outermost voxels of the object and should the densest or "thickest" portion of the object be situated at the outermost portion of the cone beam, the photon energy sensed by each detector at the outermost position of the detector array is further reduced for a voxel than that of a voxel imaged at the center of scintillation screen 27. The imaging problem becomes further aggravated as the SRAD distance becomes smaller relative to the DRAD distance. Also of significant concern is that the intensity of the radiation is a function of the total path distance of the radiation raised to some power and the path distance of the detectors at the outermost portion of the array is longer than that through the center. Accordingly, the time for the image to develop when the densest portion of the object is at the edge of the cone beam rays is materially increased or the image enhancement is weakened. Several features of the present invention are provided to overcome or minimize such problems as follows:

1) It should be noted from viewing FIGS. 8a-8c that if cross-sectional slices were taken at equal angular increments throughout the 360° rotation at both off center axes 81, 82, there will be an overlap of two dimensional images. Accordingly, it is unnecessary to record field-of-view images during the rotational angle where one of the overlaps occurs for the second and subsequent rotations. Thus, the time to complete a multiple off-center scan is less than the time it would require to complete full, equal angular field-of-view scans through 360° for each center of rotation. The overall scan time is further reduced by positioning the object on the turntable so that the volumetric portion of the highest mass density of the object is recorded in only one off-center rotation and the overlap of high volume mass densities can be skipped in subsequent off-center rotations. The encoders for the drives can be programmed based on a sample image to establish the optimum axes of rotation 81, 82. Alternatively, fixtures can be developed for turntable 24 based on the geometry of industrial object 25.

2) Referring now to FIGS. 9a and 9b, normally object 25 is rotated about a central axis extending in the y—y direction so that any off center voxel 85 would rotate as shown in FIG. 9a about a circular path (and this circular rotation would occur even for the multiple offset axis rotation shown in FIG. 8). However, for certain especially configured parts, i.e. parts elongated in one direction, and for the reasons noted above (and whether or not imaging occurs when the part is rotated only through one revolution or the part has to be translated and rotated through multiple revolutions), it is desirable to impart motion in the x—x direction to turntable 24 while the object is rotated such that the thickest portion or the greatest mass density portion of the object is spaced closest to scintillation screen 27 while the object is rotated. Thus, an otherwise off center voxel 86 positioned in the densest part of the object might move in an elliptical path about the axis of rotation such that the ellipse occurs closest to scintillation screen 27 where the field-of-view image is taken or recorded and the minor axis of the ellipse which is furthest from scintillation screen 27 is, for all intents and purposes, not within the cone beam. A path could be programmed into programmer 60 and regulated by the encoder in X drive 48. By so orientating object 25 relative to the scan geometry, the overall scan time is reduced and the image resolution enhanced.

Figure 12A:
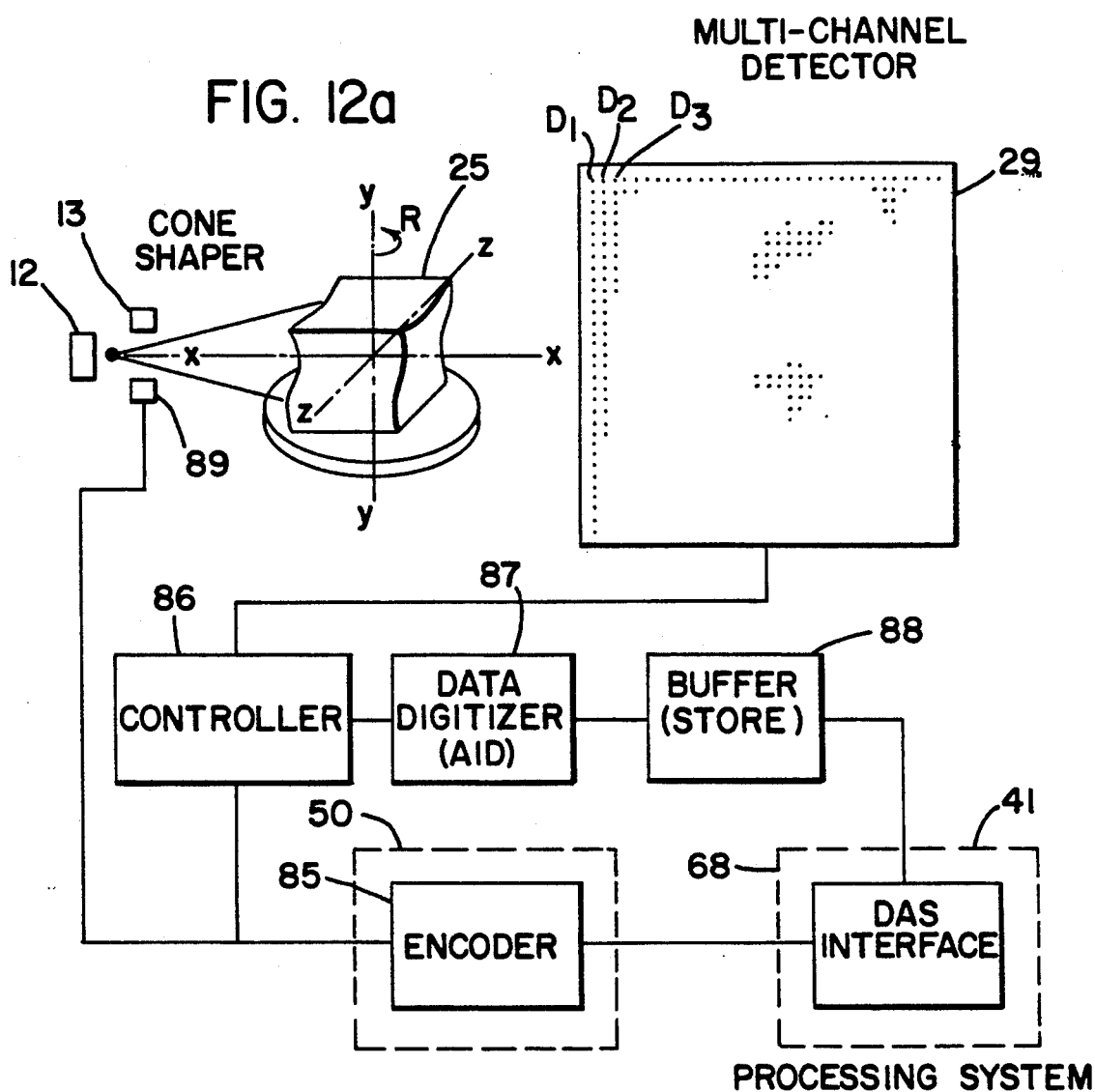
FIG. 12 illustrates schematically a portion of the system collecting X-ray data and includes FIGS. 12a, 12b and 12c.
Figure 12B:
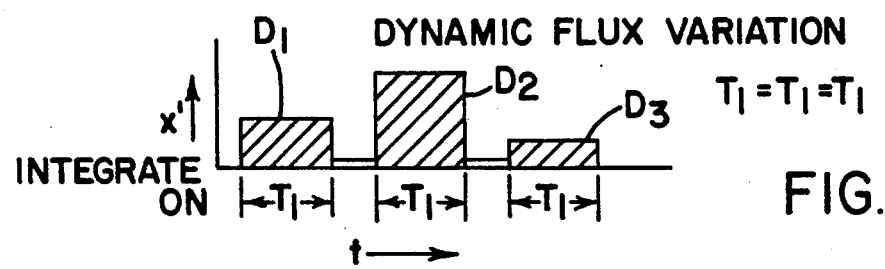

3) In conjunction with or without the optimum positioning of object 25 as discussed with references to FIGS. 8a-c and 9a-c, it is possible to dynamically vary the flux or the intensity of the hard radiation as discussed in U.S. Pat. No. 4,506,327 which issued Mar. 19, 1985, assigned to General Electric Company and incorporated by reference herein. Generally, the intensity of radiation from generator 12 is increased or decreased to correspond to the various densities of object 25. More particularly and with reference to FIG. 12a an initial scan of object 25 is taken and the readings stored in processing system 41 and used to develop a priori information. This information is then used by encoder 85 to control the intensity of radiation emitted from generator 12 and to also instruct data digitizer controller 86 when to read the X-ray data from the detector system. As indicated previously, controller 86 may be a scanning controller which scans as a raster and controls the readings of detectors in detector arrangement 29, which in FIG. 12a are, for illustration purposes, shown as individual detectors $D_1$, $D_2$, $D_3$, etc. in a multi-channel array. The analog readings of detector arrangement 29 (current, time) are serially digitized in data digitizer 87 and stored in buffer 88 which acts as a high speed memory. Because of the beam intensities required for industrial applications, the detectors D are of the current integrating type and not of the type which count photons. In accordance with the general concepts of the G.E. patent, the intensity of the emitted radiation from generator 12 is varied for each field-of-view image depending on the overall density of object 25 at that field-of-view. This permits a normalization of the integrated readings recorded by detectors D so that the sensitivity of the detectors may be optimized (i.e. readings within a narrower band) to improve resolution. However, in the G.E. patent, multiple scans of the object are required which are not necessary in the present invention. More specifically, a cone shaping mechanism 89 can be employed to vary the intensity of individual beams of radiation within the cone beam. The dynamically varied radiation beams are correlated by encoder 85 and data digitizer controller 86 to individual detectors $D_1$, $D_2$, $D_3$, etc. or to certain areas of the detectors within the multi-channel detector array. Cone shaping mechanisms are generally wedge shaped or other geometrically configured mechanisms, such as paraboloid (for example see U.S. Pat. No. 4,288,695 incorporated by reference herein) which are positionally located in a variable manner in front of the source of generator 12 to control the intensity of radiation beams or portions of beams of radiation striking individual detectors D or detector portions within detector array 29. The analog signals generated for individual detectors $D_1$, $D_2$, $D_3$, etc. is diagrammatically illustrated in the dynamic flux variation schematic of FIG. 12a. The current sensed by each detector D for a constant time period T is integrated and shown as the area under the curve for each detector which is digitized in data digitizer 87. Since the radiation beams have been varied for object density, the deviation in the signal sensed between individual detectors is significantly narrowed when compared to that which would have been sensed if no corrections were made. This permits each field-of-view image to have a sharp resolution since the range of light spectrum sensed by the detectors is "normalized" so that the sensitivity of the detectors (i.e. compensation for noise) can be optimized to improve resolution. The digitized data is then adjusted in the processing system 41 by the stored a priori information to permit accurate image construction.

4) In practice, the densities and geometries of many industrial objects 25 require high power generators operating at constant maximum power. Such applications limit the use of cone shaping mechanisms other than for purposes of correcting or normalizing the different path lengths of the radiation.

Figure 12C:
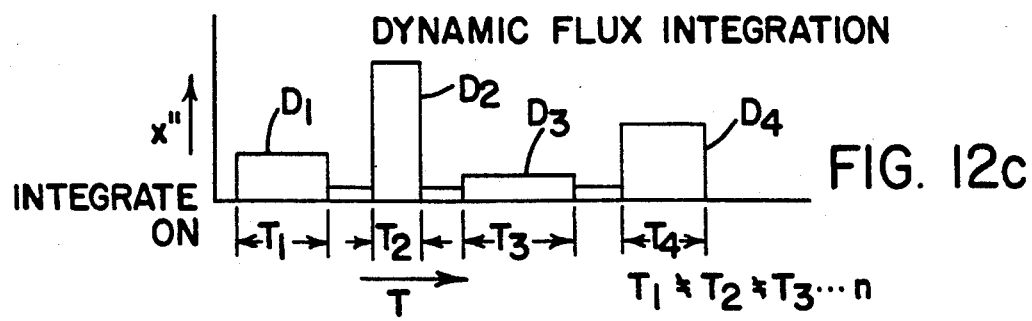

The graph entitled Dynamic Flux Integration in FIG. 12c uses the same concepts discussed with respect to Dynamic Flux Variation to develop a priori information and then utilizes the information to vary the time detectors $D_1$, $D_2$, $D_3$, etc. sense the light photons to "normalize" the analog signals developed by the detectors. As in the dynamic flux variation concept discussed in paragraph 3 above, the dynamic flux integration concept can be utilized either in the sense of varying the integration time for all detectors in different field-of-view images or varying individual detector signals within the detector array to enhance each field-of-view image. Further, it is possible to combine Dynamic Flux Integration with Dynamic Flux Variation.

In the normal batch type operation of the system as described in the arrangement shown in FIGS. 1 and 2, the R drive rotates object 25 through a discrete angle and stops and the two dimensional "digitized radiograph" is taken at that time whereupon the turntable rotates through another set angle and the digitized radiograph developed at that position. Generally speaking, 720 field-of-view images (digitized radiographs) can be taken in only 120 seconds. In the imaging process the 720 field-of-view images produce detector readings which are utilized to construct 512 cross-sectional slices of object 25 similar to that generated in the medical CT systems, i.e. usually perpendicular to an object's axis. In the system disclosed, the cross-sectional slices can be reconstructed perpendicular to any plane through the object as well as generating any two dimensional "slice" picture through any plane of the object. The number of cross-sectional slices which are reconstructed views performed by the computer utilizing appropriate algorithms can be varied to a lesser number, i.e. 256 or 128, with a corresponding reduction in the time (from 120 seconds) to construct the image—that is the time to reconstruct vis-a-vis computer 60 is the limiting factor and not the time to obtain field-of-view data) and also a corresponding lock in the resolution of the three dimensional transparent image which is reconstructed. While this is an entirely acceptable method for non-invasively inspecting geometrically complex objects on a batch type basis, there are many industrial applications where particularly critical portions of an object must be inspected for each object moving on an assembly line.

Figure 13A:
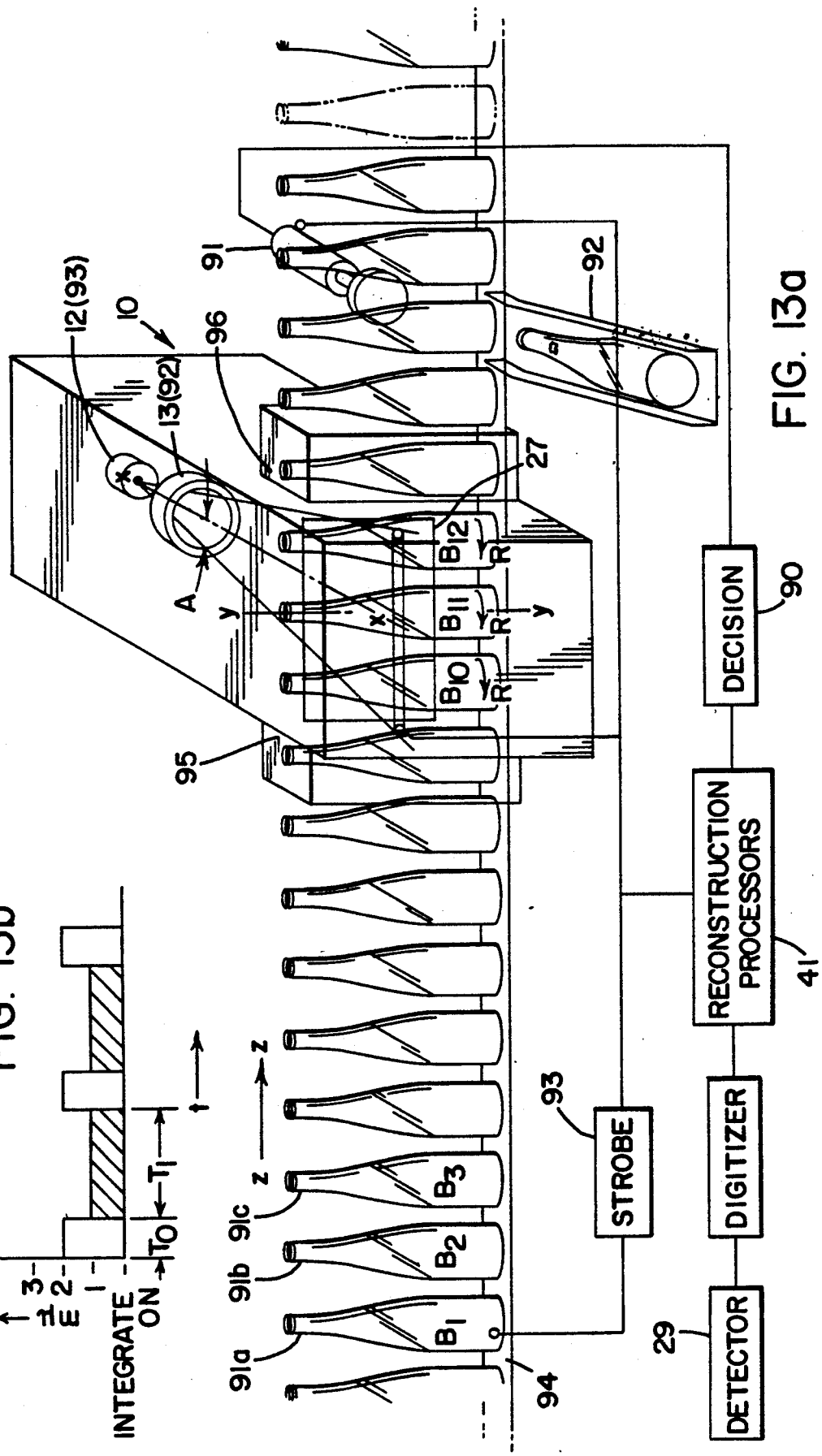
FIG. 13 schematically illustrates a specific industrial application of the system and includes FIGS. 13a and 13b.
Figure 13B:
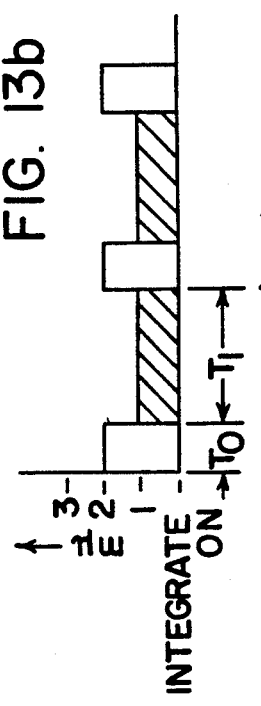

One typical application would be the inspection of the neck portion of bottles in a bottle manufacturing facility. In such applications, line speed is typically between 150 and 250 feet per minute with a slight spacing between the bottles. On the other hand, only a portion of the neck of a bottle is critical to the bottle inspection and the neck density of the bottle is relatively low and somewhat constant. Accordingly, relatively few 2-dimensional views, typically 36 per revolution, need be taken to develop sufficient acceptance/rejection parameters. As shown in FIG. 13a, this is accomplished by providing a plurality of scintillation screens 27 which are aligned with the necks of bottles $B_1$, $B_2$, $B_3$ moving past the screens in an assembly line fashion and which receive radiation preferably from one x-ray generator source 12. A belt arrangement 94 positioned below scintillation screens 27 engages the body portions of bottles B and is tensioned so that each bottle $B_1$, $B_2$, etc., is rotated at a constant rate through one complete revolution from the point that each bottle enters the scintillation screen arrangement at its entry end 95 to the point where each bottle exits the scintillation screen arrangement at its exit end 96. The entire bottling line, at least at the point where the bottles B enter entry end 95 to the rejection point 91 where defective bottles are removed from the bottling line by a reject chute 92, is timed by a strobe light 93 or similar counter so that each bottle $B_1$, $B_2$, etc. is individually identified. As shown in FIG. 13a, strobe 93 is correlated to belt 94 and the line speed to instruct controller 86 to read the detector arrangement 29. As shown in the integration graph of FIG. 13b, the analog signal is integrated during a very short "on" time because the bottle has a relatively low density at its neck portion. This "on" time $T_0$ is in the range of 2-3 milliseconds compared to an "on" time in the range of 100 milliseconds or so for fairly dense objects irradiated in scan enclosure 10 on a "batch" process basis. The data is then digitized in A/D device 87 and stored in buffer 88 during the read data time $T_1$. At the bottle line speeds discussed, the bottle travels between 10 to 20 thousandths of an inch during $T_0$. Thus, the resolution capability or defect size which the system is able to ascertain (voxel size) is limited to 10 to 20 thousandths of an inch and preferably is double the $T_0$ distance, i.e. 0.020 to 0.040". During the time bottles $B_1$, $B_2$, $B_3$, are within scan enclosure 10, multiple scintillation screens 27 are effective to record one field-of-view simultaneously for the number of bottles within the path of the cone beam. The composite field-of-view image for multiple bottles B is then simultaneously processed by the reconstruction processors 41 to further reduce the image reconstruction time. That is, the 120 second time to process 512 slices is reduced by that time to process only 36 slices and that time is further effectively reduced by the number of bottles simultaneously irradiated through multiple detector screens 29. The image reconstruction process occurs during the time the bottles leave exit end 96 and the time they enter reject station 91 and the distance therebetween is determined by the bottle line speed. Because identity of the individual bottles has been maintained, a permanent CT record of each rejected bottle can be maintained, etc. which will be of significant value to the manufacturing process.

The invention has been described with reference to a preferred embodiment. Obviously alterations and modifications will occur to others upon a reading and understanding of the specification. It is our intention to include all such modifications and alterations insofar as they come within the scope of the present invention.

It is thus the essence of the invention to provide an improved industrial CT system based on an area detector recording digitized radiographs as the object is rotated only about one axis and in which the image resolution is enhanced while the scan time is materially decreased by correcting for the geometry of the irradiated object.

Having thus defined my invention, we claim:

1. A computerized tomographic industrial radiation system for constructing a three dimensional transparent image of at least a portion of an object comprising:

a point source generator for generating a non-pulsed, three dimensional cone beam of emitted rays of hard radiation;

collimator means associated with said point source generator for controlling the three dimensional cone beam angle and the peripheral configuration of said three dimensional cone beam;

positioning means for locating said object in the path of said three dimensional cone beam such that a predetermined volumetric portion of said object is exposed to said three dimensional cone beam of hard radiation for attenuation of the radiation passing through said object;

two dimensional detector means fixed with respect to said point source generator and located on the opposite side of said object from said point source generator for recording the attenuated radiation, said two dimensional detector means including a scintillation screen for receiving said attenuated radiation and converting said attenuated radiation through said scintillation screen into a two dimensional shadow image;

digitizing means for converting said two dimensional shadow image into an ordered array of digitized numbers from analog signals initially generated by said two dimensional detector means, each digitized number in said ordered array corresponding to the energy level of an attenuated beam of radiation at a given location in said ordered array;

said positioning means including means for positioning said object in a three dimensional relationship relative to said point source generator and means for intermittently rotating said object relative to said point source generator and said two dimensional detector means about only one axis of said object through predetermined angular increments, said axis centered at said predetermined volumetric portion;

means for recording said digitized numbers during the time said means for intermittently rotating is unactuated;

imaging means for constructing a three dimensional transparent image of said predetermined volumetric portion from said digitized numbers after a predetermined number of angular rotations whereby said three dimensional image can be constructed;

said point source generator is centered along an x axis and situated at a predetermined distance from said object and operable to produce a plurality of emitted beams of radiation emanating from said point source generator in generally straight lines which define a three dimensional fan shaped array of emitted radiation beams;

said scintillation screen centered with respect to said x axis and extending along a y axis and a z axis perpendicular to one another and to said x axis for generating visible light in response to the energy level of attenuated radiation beams impacting thereon;

a plurality of detectors arranged in a generally ordered array correlated in a position to said y axis and z axis, each detector operable to generate an analog signal indicative of the light energy transmitted thereto from said scintillation screen;

said imaging means further effective to store a priori information related to said analog signal during an initial rotation of said object; and dynamic flux integration means for narrowing the variation between the analog signals generated by said detectors within said ordered array between various rotational positions of said object to enhance the resolution of the image produced by said imaging means, said dynamic flux integration means including means for integrating over a time period said analog signals generated by said detectors and means for varying said time period actuated by said imaging means in accordance with said a priori data and correlated to the mass density of said object at any given angular rotation such that a longer integrating time is provided when the mass density of said object penetrated by said hard radiation over a predetermined volumetric portion of said object is higher than the mass density of said object at another predetermined volumetric portion, and said imaging means further correlated to said positioning means to adjust the digitized numbers of said detectors in response to the variation in the time of integration.

2. The system of claim 1 further including dynamic flux variation means effective to uniformly vary the intensity of transmitting beams of radiation which strike as attenuated beams of radiation said scintillation screen in said y and z direction, said intensity of said beams correlated said a priori information from said imaging means to account for the mass density of said object along said x axis as said object rotates about a y axis such that the intensity of the transmitting beams passing through high mass densities of said object at a specific angular rotation is higher than the beam intensity passing through low mass portions of said object at a different angular rotation whereby the energy levels of the attenuated beams striking said scintillation screen are at a lesser variance than that which would occur had the intensity of said transmitting beams been uniform; and
said imaging means correlated to said dynamic flux variation means and effective to adjust said digitized numbers in accordance with the variation in intensity of said transmitting beams of radiation.

3. The system of claim 2 wherein said detector means includes a two dimensional detector array developing a plurality of analog signals, each analog signal indicative of the energy of the light photons emitted from said scintillation screen at discrete locations in said detector array; and
said object is positioned by said positioning means to rotate along a predetermined path about an axis extending through said object such that the object is positioned closest to said scintillation screen when said three dimensional cone beam passes through the largest mass volume portion of said object.

4. The system of claim 3 wherein said means for intermittently rotating is effective to rotate said object along a generally elliptical path between said point source generator and said two dimensional detector means, said elliptical path having, by definition, a major axis and a minor axis, said major axis correlated to the largest diametrical distance through the object and said minor axis correlated to the smallest diametrical distance through said object whereby said two dimensional detector means is not subjected to variations in light intensity otherwise possible during its rotation to improve image resolution; and means associated with said means for intermittently rotating and said digitizing means to correct said digitized numbers for the distance of said generally elliptical path.

5. A computerized tomographic industrial radiation system for constructing a three dimensional transparent image of at least a portion of an object comprising:
a point source generator for generating a non-pulsed, three dimensional cone beam of emitted rays of hard radiation;
collimator means associated with said point source generator for controlling the three dimensional cone beam angle and the peripheral configuration of said three dimensional cone beam;
positioning means for locating said object in the path of said three dimensional beam such that a predetermined volumetric portion of said object is exposed to said three dimensional cone beam of hard radiation for attenuation of the radiation passing through said object;
two dimensional detector means fixed with respect to said point source generator and located on the opposite side of said object from said point source generator for recording the attenuated radiation, said two dimensional detector means including a scintillation screen for receiving said attenuated radiation and converting said attenuated radiation through said scintillation screen into a two dimensional shadow image;
digitizing means for converting said two dimensional shadow image into an ordered array of digitized numbers, each digitized number in said ordered array corresponding to the energy level of an attenuated beam of radiation at a given location in said ordered array;
said positioning means including means for positioning said object in a three dimensional relationship relative to said point source generator and means for intermittently rotating said object relative to said point source generator and said two dimensional detector means about only one axis of said object through a predetermined angular increments, said axis centered at said predetermined volumetric portion;
means for recording said digitized numbers during the time said means for intermittently rotating is unactuated;
imaging means for constructing a three dimensional transparent image of said predetermined volumetric portion from said digitized numbers after a predetermined number of angular rotations whereby said three dimensional image can be constructed;
said two dimensional detector means includes a two dimensional detector array developing a plurality of analog signals, each signal indicative of the energy of the light photons emitted from said scintillation screen at discrete locations in said detector array;
said object is positioned by said positioning means to rotate along a predetermined path about an axis extending through said object such that the object is positioned closest to said scintillation screen when said three dimensional cone beam passes through the largest mass volume portion of said object;
said means for intermittently rotating is effective to rotate said object along a generally eccentric, non-circular path between said point source generator and said two dimensional detector means, said eccentric path having a major axis and a minor axis, said major axis correlated to the largest diametrical distance through the object and said minor axis correlated to the smallest diametrical distance through said object whereby said two dimensional detector means is not subjected to variations in light intensity which is otherwise possible during circular rotation to improve image resolution; and controller means associated with said means for intermittently rotating and said digitizing means as well as said point source generator and said collimator means to correct said digitized numbers for the geometrically offset center distances of said generally eccentric path.

6. The system of claim 5 wherein said means for intermittently rotating is effective to rotate said object along a generally elliptical path between said point source generator and said two dimensional detector means.

7. A computerized tomographic industrial radiation system for constructing a three dimensional transparent image of at least a portion of an object comprising:

a point source generator for generating a non-pulsed, three dimensional cone beam of emitted rays of hard radiation;

collimator means associated with said point source generator for controlling the three dimensional cone beam angle and the peripheral configuration of said three dimensional cone beam;

positioning means for locating said object in the path of said three dimensional cone beam such that a predetermined volumetric portion of said object is exposed to said three dimensional cone beam of hard radiation for attenuation of the radiation passing through said object;

two dimensional detector means fixed with respect to said point source generator and located on the opposite side of said object from said point source generator for recording the attenuated radiation, said two dimensional detector means including a scintillation screen for receiving said attenuated radiation and converting said attenuated radiation through said scintillation screen into a two dimensional shadow image;

digitizing means for converting said two dimensional shadow image into an ordered array of digitized numbers, each digitized number in said ordered array corresponding to the energy level of an attenuated beam of radiation at a given location in said ordered array;

said positioning means including means for positioning said object in a three dimensional relationship relative to said point source generator and means for intermittently rotating said object relative to said point source generator and said two dimensional detector means about only one axis of said object through predetermined angular increments, said axis centered at said predetermined volumetric portion;

means for recording said digitized numbers during the time said means for rotating is unactuated;

imaging means for constructing a three dimensional transparent image of said predetermined volumetric portion from said digitized numbers after a predetermined number of angular rotations whereby said three dimensional image can be constructed; and said object has at least two cross-sectional areas in any two dimensional planes orthogonal to one another each of which is greater than the area of said scintillation screen;

said positioning means operative to i) position said object so that said three dimensional cone beam initially passes through a first portion of the peripheral surface of said object, ii) actuate said means for intermittently rotating to rotate said object about a first axis which is offset from the center of said object through only one revolution, iii) translate said object along at least one of the plane axis so that the three dimensional cone beam passes through a second portion of the peripheral surface of said object and iv) actuate said means for intermittently rotating to rotate said object through only one revolution about a second axis whereby said imaging means is effective to construct a three dimensional image of the entire object.

8. The system of claim 7 wherein said two dimensional detector means includes a two dimensional detector array developing a plurality of analog signals, each analog signal indicative of the energy of the light photons emitted from said scintillation screen at discrete locations in said detector array; and said object is positioned by said positioning means to rotate along a predetermined path about an axis extending through said object such that the object is positioned closest to said scintillation screen when said three dimensional cone beam passes through the largest mass volume portion of said object.

9. The system of claim 8 wherein said object is positioned by said positioning means to rotate about said axis extending through said object which is parallel to the plane containing said scintillation screen in a non-circular path such that the largest mass volume portion of said object is closest to said scintillation screen as said object is rotated through one revolution about one of its axes.

10. A computerized tomographic industrial radiation system for constructing a three dimensional transparent image of at least a portion of an object comprising:

a point source generator for generating a non-pulsed, three dimensional cone beam of emitted rays of radiation;

collimator means associated with said point source generator for controlling the three dimensional cone beam angle and the peripheral configuration of said three dimensional cone beam;

positioning means for locating said object in the path of said three dimensional cone beam such that a predetermined volumetric portion of said object is exposed to said three dimensional cone beam of radiation for attenuation of the radiation passing through said object;

two dimensional detector means fixed with respect to said point source generator and located on the opposite side of said object from said point source generator for recording the attenuated radiation, said two dimensional detector means including a scintillation screen for receiving said attenuated radiation and converting said attenuated radiation through said scintillation screen into a two dimensional shadow image;

digitizing means for converting said two dimensional shadow image into an ordered array of digitized numbers, each digitized number in said ordered array corresponding to the energy level of an attenuated beam of radiation at a given location in said ordered array;

said positioning means including means for positioning said object in a three dimensional relationship relative to said point source generator and means for intermittently rotating said object relative to said point source generator and said two dimensional detector means about only one axis of said object through predetermined angular increments, said axis centered at said predetermined volumetric portion;

means for recording said digitized numbers during the time said means for intermittently rotating is unactuated;

imaging means for constructing a three dimensional transparent image of said predetermined volumetric portion from said digitized numbers after a predetermined number of angular rotations whereby said three dimensional image can be constructed;

said two dimensional detector means includes a two dimensional detector array developing a plurality of analog signals, each analog signal indicative of the energy of the light photons emitted from said scintillation screen at discrete locations in said detector array;

said object is positioned by said positioning means to rotate along a predetermined path about an axis extending through said object such that the object is positioned closest to said scintillation screen when said three dimensional cone beam passes through the largest mass volume portion of said object; and said means for intermittently rotating is effective to rotate said object along a generally eccentric, noncircular path between said point source generator and said two dimensional detector means, said eccentric path having a major axis and a minor axis, said major axis correlated to the largest diametrical distance through the object and said minor axis correlated to the smallest diametrical distance through said object whereby said two dimensional detector means is not subjected to variations in light intensity which is otherwise possible during circular rotation to improve image resolution;

controller means associated with said means for intermittently rotating and said digitizing means as well as said point source generator and said collimator means to correct said digitized numbers for the geometrically offset center distances of said generally eccentric path;

said system is oriented along x, y, and x axes perpendicular to one another with orthogonal planes passing through any two of said axes;

said scintillation screen is situated in a plane passing through the y-z axis and having y and z dimensions extending along said y axis and said z axis respectively, said x axis intersecting the y-z plane at a center point thereof, said point source generator having a point source of a finite diametrical distance equal to FSS, said point source generator situated on said x axis and extending on one side from the axis of rotation of said object a distance equal to SRAD, said scintillation screen positioned on the opposite side of said object having a distance on said x axis from said object's axis of rotation equal to DRAD;

said two dimensional detector means capable of recording discrete areas of light emanating from said scintillation screen correlated to said ordered array, each discrete area having a maximum detector resolution distance, DS, extending in the y-z plane;

said positioning means effective to initially position said object between said point source generator and said scintillation screen such that said two dimensional shadow image produced by said two dimensional detector means represents a substantial cross-sectional area of said object in a two-dimensional spatial relationship, said positioning means further including a zoom means for viewing a discrete volumetric portion of said object at a sharper resolution than an initially established with the limits of said sharper resolution defined as the smallest discrete volumetric portion within said discrete volumetric portion which can be imaged, said smallest discrete volumetric portion having a maximum dimension, R, defined by a plane extending therethrough, said zoom means centering said discrete volumetric portion at said axis of rotation at said SRAD-DRAD distances, dependent upon a predetermined desired resolution, R, which is the largest SRAD distance established by the equations $$R = \frac{DS \times SRAD}{SRAD + DRAD} \text{ and}$$

$$R = \frac{FS \times DRAD}{SRAD + DRAD}.$$

11. A computerized tomographic industrial radiation system for sampling a plurality of continually moving objects and rapidly constructing a three dimensional transparent image of a portion of each moving object so that acceptance-rejection decisions of said objects can be made, said system comprising:

a point source generator for generating a non-pulsed, three-dimensional cone beam of emitted rays of hard radiation;

collimator means associated with said point source generator for controlling the three dimensional cone beam angle and the peripheral configuration of said three dimensional cone beam so that a plurality of objects can be simultaneously irradiated;

positioning means for locating said objects in the path of said three dimensional cone beam such that a predetermined volumetric portion of each object is exposed to said three dimensional cone beam of hard radiation for attenuation of the radiation passing through said object;

two dimensional means fixed with respect to said point source generator and located on the opposite side of said objects for recording the attenuated radiation, said two dimensional detector means including a scintillation screen dimensionally sized to span a plurality of objects and receiving attenuated radiation and converting said radiation through said scintillation screen into two dimensional shadow images of said plurality of objects;

digitizing means for converting said two dimensional shadow image into an ordered array of digitized numbers, said digitized number in said ordered array corresponding to the energy level of an attenuated beam of radiation at a given location in said ordered array;

said positioning means including means for positioning said objects relative to said point source generator and means for rotating said objects relative to said point source generator and said two dimensional detector means about only one axis of said objects through a minimum number of predetermined angular increments when said objects move by said detector means;

means for recording said digitized numbers while said objects are rotating and linearly moving past said two dimensional detector means and including timing means correlated to the speed and rotation of said objects and actuating said digitizing means in an on/off manner to record a limited number of attenuated radiation beams corresponding to said number of predetermined increments; and imaging means for constructing a three dimensional transparent image of said predetermined volumetric portion from said digitized numbers after a predetermined number of angular rotations whereby said three dimensional image can be constructed.

12. A computerized tomographic industrial radiation system for constructing a three dimensional transparent image of at least a portion of an object comprising:

a point source generator for generating a non-pulsed, three dimensional cone beam of emitted rays of hard radiation;

collimator means associated with said generator for controlling the three dimensional cone beam angle and the peripheral configuration of said three dimensional cone beam;

positioning means for locating said object in the path of said three dimensional cone beam such that a predetermined volumetric portion of said object is exposed to said three dimensional cone beam of hard radiation for attenuation of the radiation passing through said object;

two dimensional detector means fixed with respect to said point source generator and located on the opposite side of said object for recording the attenuated radiation, said two dimensional detector means including a scintillation screen receiving said attenuated radiation and converting said attenuating radiation through said scintillation screen into a two dimensional shadow image;

digitizing means for converting said two dimensional shadow image into an ordered array of digitized numbers, each digitized number in said ordered array corresponding to the energy level of an attenuated beam of radiation at a given location in said ordered array;

said positioning means including means for positioning said object in a three dimensional relationship relative to said point source generator and means for intermittently rotating said object relative to said point source generator and said two dimensional detector means about only one axis of said object through predetermined angular increments, said axis centered at said predetermined volumetric portion;

means for recording said digitized numbers during the time said intermittently rotating means is unactuated;

imaging means for constructing a three dimensional transparent image of said predetermined volumetric portion from said digitized numbers after a predetermined number of angular rotations whereby said three dimensional image can be constructed;

wherein said system is oriented along x, y and z axes perpendicular to one another with orthogonal planes passing through any two of said axes;

said scintillation screen is situated in a plane passing through said y-z axis and having y and z dimensions extending along said y axis and said z axis respectively, said x axis intersecting said y-z plane at a center point thereof, said point source generator having a point source of a finite diametrical distance equal to FSS, said point source generator situated on said x axis and extending on one side from the axis of rotation of said object having a distance equal to SRAD, said scintillation screen positioned on the opposite side of said object having a distance on said x axis measuring from said object's axis of rotation equal to DRAD, said two dimensional detector means capable of recording discrete areas of light emanating from said scintillation screen correlated to said ordered array, each discrete area of light having a maximum detector resolution distance, DS, extending in the y-z plane;

said positioning means effective to initially position said object between said point source generator and said scintillation screen such that said two dimensional shadow image produced by said two dimensional detector means represents a substantial cross-sectional area of said object in a two-dimensional spatial relationship, said positioning means further including zoom means for viewing a discrete volumetric portion of said object at a sharper resolution than that initially established with the limits of said sharper resolution defined as the smallest discrete volumetric portion within said discrete volumetric portion which can be imaged, said smallest discrete volumetric portion having a maximum dimension, R, defined by a plane extending therethrough, said zoom means centering said discrete volumetric portion at said object's axis of rotation at said SRAD and DRAD distances, dependent upon a predetermined desired resolution, R, which is a largest SRAD distance established by the equations $$R = \frac{DS \times SRAD}{SRAD + DRAD} \text{ and}$$

$$R = \frac{FS \times DRAD}{SRAD + DRAD}.$$

13. A computerized tomographic industrial radiation system for constructing a three dimensional transparent image of at least a portion of an object comprising:

a point source generator for generating a three dimensional cone beam of emitted rays of radiation;

collimator means associated with said point source generator for controlling the three dimensional cone beam angle and the peripheral configuration of said three dimensional cone beam;

positioning means for locating said object in the path of said three dimensional cone beam such that a predetermined volumetric portion of said object is exposed to said three dimensional cone beam of radiation for attenuation of radiation passing through said object;

two dimensional detector means fixed with respect to said point source generator and located on the opposite side of said object from said point source generator for recording the attenuated radiation transmitted from said object, said two dimensional detector means including a scintillation device for receiving said attenuated radiation and converting said attenuated radiation through said scintillation device into a two dimensional shadow image;

digitizing means for converting said two dimensional shadow image into an ordered array of digitized numbers, each digitized number in said ordered array corresponding to the energy level of an attenuated beam of radiation at a given location in said ordered array;

said positioning means including means for rotating said object about an axis extending through said object along a generally eccentric non-circular path between said point source generator and said two dimensional detector means whereby the object is positioned closest to said scintillation device when said three dimensional cone beam passes through a largest mass volume portion of a predetermined volumetric portion of said object.

14. The system of claim 13 wherein said three dimensional cone beam is non-pulsed.

15. The system of claim 14 where said positioning means includes means for intermittently rotating said object relative to said point source generator.

16. The system of claim 14 wherein said point source generator is centered along an x axis and situated at a predetermined distance from said object and operable to produce a plurality of emitted beams of radiation emanating from said point source generator in generally straight lines which define a three dimensional fan shaped array of emitted radiation beams;

said scintillation device is centered with respect to an x axis and extending along a y axis and a z axis perpendicular to one another and to said x axis for generating visible light in response to the energy level of said attenuated radiation impacting thereon; and said two dimensional detector means comprising a plurality of detectors arranged in a generally ordered array correlated in a position defined by a said y and z axis, each of said detectors to operable to generate an analog signal indicative of the light energy transmitted thereto from said scintillation device.

17. A method of constructing a three dimensional transparent image of at least a portion of an object comprising the steps of:

generating a three dimensional cone beam of emitted rays of radiation;

providing a scintillation screen;

controlling the three dimensional cone beam angle and the peripheral configuration of said three dimensional cone beam such that substantially the entire area of the three dimensional cone beam strikes the scintillation screen;

locating said object in the path of said three dimensional cone beam such that an axis centered through a selected volumetric portion of said object to be scanned will be perpendicular to an x axis which intersects the center of the three dimensional cone beam and the scintillation screen;

moving the object with respect to the scintillation screen whereby the attenuated radiation transmitted from the object in response to exposure to the three dimensional cone beam of radiation encompasses the scintillation screen;

rotating said object relative to said three dimensional cone beam of emitted rays of radiation about a centered axis of a predetermined volumetric portion;

recording the attenuated radiation transmitted from said object from the opposite side of said object in the path of the three dimensional cone beam;

converting said attenuated radiation through a scintillation screen into an ordered array of digitized numbers each corresponding to the energy level of an attenuated beam of radiation at a given location in said ordered array; and constructing an initial three dimensional transparent image of said predetermined volumetric portion from said digitized numbers.

18. The method of claim 17 further including the step of repositioning said object in the path of said three dimensional cone beam such that the distance from an axis of rotation through the object to the scintillation screen is positioned closest to said scintillation screen when the mass volume of the object is at a maximum.

19. The method of claim 18 including the step of rotating said object intermittently with respect to said three dimensional cone beam of emitted rays subsequent to said step of repositioning said object.

20. The method of claim 19 wherein said step of rotating said object subsequent to said step of repositioning includes the step of rotating said object intermittently about a second axis offset from said centered axis in a generally eccentric, non-circular path.

21. The method of claim 20, including the steps of:

recording the attenuated radiation from the opposite side of said object in the path of the three dimensional cone beam subsequent to said step of repositioning;

converting said attenuated radiation through said scintillation screen into an ordered array of digitized numbers each corresponding to the energy level of an attenuated beam of radiation at a given location in said ordered array;

constructing a three dimensional transparent image of said predetermined volumetric portion from said digitized numbers after a predetermined number of angular rotations subsequent to repositioning.

22. The method of claim 17 wherein said step of rotating subsequent to said step of repositioning includes rotating said object 360 degrees about said centered axis.

23. The method of claim 20 wherein the step of rotating subsequent to said step of repositioning includes rotating said object 360 degrees about the second axis.

* * * * *